(12) United States Patent
Sheldon et al.

(10) Patent No.: US 7,809,440 B2
(45) Date of Patent: Oct. 5, 2010

(54) METHODS AND APPARATUS FOR DETECTING VENTRICULAR DEPOLARIZATIONS DURING ATRIAL PACING

(75) Inventors: Todd J. Sheldon, North Oaks, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1215 days.

(21) Appl. No.: 10/359,986

(22) Filed: Feb. 6, 2003

(65) Prior Publication Data

US 2004/0158292 A1 Aug. 12, 2004

(51) Int. Cl.
*A61N 1/362* (2006.01)

(52) U.S. Cl. ............................................. 607/9; 607/14

(58) Field of Classification Search ...................... 607/9, 607/14, 15, 28, 13
See application file for complete search history.

(56) References Cited

U.S. PATENT DOCUMENTS

| 3,949,758 | A | 4/1976 | Jirak |
| 4,310,000 | A | 1/1982 | Lindemans |
| 4,428,378 | A | 1/1984 | Anderson et al. |
| 4,549,548 | A | 10/1985 | Wittkampf et al. |
| 4,585,004 | A | 4/1986 | Brownlee |
| 4,674,508 | A | 6/1987 | DeCote |
| 4,686,988 | A | 8/1987 | Sholder |
| 4,727,877 | A | 3/1988 | Kallok |
| 4,729,376 | A | 3/1988 | DeCote, Jr. |
| 4,759,366 | A | 7/1988 | Callaghan |
| 4,788,980 | A | 12/1988 | Mann et al. |
| 4,825,870 | A | 5/1989 | Mann et al. |
| 4,858,610 | A | 8/1989 | Callaghan et al. |
| 4,890,617 | A | 1/1990 | Markowitz et al. |
| 4,958,632 | A | 9/1990 | Duggan |
| 5,003,975 | A | 4/1991 | Hafelfinger et al. |
| 5,097,832 | A | 3/1992 | Buchanan |
| 5,117,824 | A | 6/1992 | Keimel et al. |
| 5,144,949 | A | 9/1992 | Olson |
| 5,324,310 | A | 6/1994 | Greeninger et al. |
| 5,331,966 | A | 7/1994 | Bennett et al. |
| 5,447,519 | A | 9/1995 | Peterson |
| 5,601,615 | A * | 2/1997 | Markowitz et al. ............ 607/28 |

(Continued)

FOREIGN PATENT DOCUMENTS

EP 0451498 B1 3/1991

(Continued)

*Primary Examiner*—Scott M Getzow
*Assistant Examiner*—Joseph M Dietrich
(74) *Attorney, Agent, or Firm*—Stephen W. Bauer

(57) ABSTRACT

AV synchronous, dual chamber pacing systems are disclosed having improved sensing of ectopic ventricular depolarizations or PVCs coincidentally occurring at or shortly following delivery of an A-PACE pulse. A first ventricular sense amplifier that is blanked during and following delivery of an A-PACE pulse is coupled to active and indifferent ventricular pace/sense electrodes defining a ventricular sense vector for sensing natural ventricular depolarizations and declaring a V-EVENT. A far field PVC sense amplifier coupled to a far field PVC sense electrode pair defining a PVC sense vector detects such PVCs while the ventricular sense amplifier is blanked. A PVC declared during the ventricular blanking period by the far field PVC sense amplifier is employed to deliver a VSP pulse upon time-out of a VSP delay, if the VSP function is provided and programmed ON, and/or to halt time-out of an AV delay.

27 Claims, 10 Drawing Sheets

U.S. PATENT DOCUMENTS

| | | | |
|---|---|---|---|
| 5,626,623 A | 5/1997 | Kieval et al. | |
| 5,683,431 A | 11/1997 | Wang | |
| 5,755,742 A | 5/1998 | Schuelke et al. | |
| 5,902,324 A | 5/1999 | Thompson et al. | |
| 6,128,532 A | 10/2000 | Stoop et al. | |
| 6,311,088 B1 | 10/2001 | Betzold et al. | |
| 6,317,633 B1 * | 11/2001 | Jorgenson et al. | 607/28 |
| 6,324,425 B1 * | 11/2001 | Blow et al. | 607/13 |
| 6,477,415 B1 | 11/2002 | Yerich et al. | |
| 6,819,955 B2 * | 11/2004 | Levine | 607/28 |
| 7,260,432 B2 * | 8/2007 | Kramer et al. | 607/9 |

FOREIGN PATENT DOCUMENTS

EP          451498 B1 *  2/1995

* cited by examiner

METHODS AND APPARATUS FOR DETECTING VENTRICULAR DEPOLARIZATIONS DURING ATRIAL PACING

RELATED APPLICATIONS

This disclosure is related to the following co-pending U.S. patent application Ser. No. 11/260,984, filed Sep. 30, 2002, entitled "METHOD AND APPARATUS FOR PERFORMING STIMULATION THRESHOLD SEARCHES" by C. M. Manrodt et al., which is not admitted as prior art with respect to the present disclosure by its mention in this section.

FIELD OF THE INVENTION

This invention relates to implantable AV synchronous, dual chamber pacing systems, and particularly to improved sensing of ectopic ventricular depolarizations coincidentally occurring at or shortly following delivery of an atrial pacing pulse.

BACKGROUND OF THE INVENTION

Atrial synchronized, dual chamber, pacing modes, particularly, the multi-programmable, VDD, VDDR, DDD and DDDR pacing modes, have been widely adopted in implantable dual chamber pacemakers for providing atrial and ventricular or AV synchronized pacing on demand. Such dual chamber pacing modes have also been incorporated into implantable cardioverter/defibrillators (ICDs) and into right and left heart pacing systems providing synchronized right and left heart pacing for enhancing left ventricular cardiac output as described in commonly assigned U.S. Pat. No. 5,902,324.

Such pacing systems are embodied in an implantable pulse generator (IPG) adapted to be subcutaneously implanted and at least atrial and ventricular pacing or cardioversion/defibrillation leads that are coupled to the IPG. The atrial and ventricular leads each incorporate one or more lead conductor that extends through the lead body to an exposed pace/sense electrode or cardioversion/defibrillation electrode disposed in operative relation to a heart chamber. Typically, a negative-going or cathodal voltage pacing pulse is applied through a pacing path comprising a small surface area, active pace/sense electrode (also characterized as a cathode electrode) and a relatively larger surface area, return or indifferent pace/sense electrode (also characterized as an anode electrode) to pace a heart chamber.

Such leads are typically characterized as unipolar leads if they comprise only a single active pace/sense electrode and/or a cardioversion/defibrillation electrode. In the pacing context, a unipolar lead is coupled with a unipolar IPG, wherein the electrically conductive IPG housing or "can" comprises a return or indifferent pace/sense electrode or anode electrode. Unipolar pacing and sensing takes place between the lead-borne active pace/sense electrode and the housing indifferent pace/sense electrode. A bipolar lead comprises at least two lead conductors coupled to a bipolar IPG and extending to an active pace/sense electrode, typically located at the distal end of the lead body, and an indifferent pace/sense electrode, typically located on the lead body proximal to the distal active pace/sense electrode. Bipolar pacing and sensing takes place between the lead-borne active pace/sense electrode and indifferent pace/sense electrode. In the bipolar configuration, the indifferent pace/sense electrode is usually a ring-like structure, referred to as the "ring" electrode, located proximal to the distal active pace/sense electrode, by about 0.5 cm to 2.5 cm. In this context, bipolar and unipolar sensing may also be referred to as "near-field" and "far-field" sensing, respectively. (Although "far-field" usually denotes sensing outside the chamber of interest, and the unipolar signal derived from such a unipolar pace/sense electrode pair is dominated by the near-field tip electrode signal.)

A pacing IPG capable of pacing in atrial synchronized modes typically includes atrial and ventricular sense amplifiers, atrial and ventricular pace pulse generators or "amplifiers", an operating system governing pacing and sensing functions, and components as described further herein in relation to a preferred embodiment of the invention.

In the typical dual chamber DDD pacing system, an atrial pacing (A-PACE) pulse generated by the atrial pace pulse generator is applied to the right atrial active and indifferent pace/sense electrodes to cause the right and left atria to depolarize. Similarly, a ventricular pacing (V-PACE) pulse generated by the ventricular pulse generator is applied to the right ventricular active and indifferent pace/sense electrodes to cause the right and left ventricles to depolarize. In more recently developed right and left heart pacing systems, pacing pulse generators and leads are incorporated into the pacing system to provide A-PACE and/or V-PACE pulses to the left atrium and/or ventricle.

The atrial sense amplifier is coupled to atrial active and indifferent pace/sense electrodes to detect electrical signals of the heart associated with atrial depolarizations (P-waves) and to generate an atrial sense event (A-EVENT) signal when detection criteria are met. The ventricular sense amplifier is coupled to ventricular active and indifferent pace/sense electrodes to detect electrical signals of the heart associated with ventricular depolarizations (R-waves) and to generate a ventricular sense event (V-EVENT) signal when detection criteria are met.

The pacing operating system times out various intervals from each A-EVENT, V-EVENT, A-PACE, and V-PACE to maintain synchronous depolarizations of the atria and ventricles. Such AV synchronous pacemakers that perform this function have the capability of tracking the patient's natural sinus rhythm and preserving the hemodynamic contribution of the atrial contraction over a wide range of heart rates. Maintenance of AV mechanical synchrony is of great importance as set forth in greater detail in commonly assigned U.S. Pat. No. 5,626,623.

Typically, the IPG operating system comprises a microcomputer controlled, digital controller/timer circuit that defines and times out a V-A interval (in DDD and DDDR modes) or a V-V interval (in VDD and VDDR modes) upon a V-EVENT or V-PACE pulse and times out an AV delay in response to an A-EVENT (in VDD, VDDR, DDD, DDDR modes) or in response to an A-PACE pulse (in DDD and DDDR modes) as well as a number of other intervals. An SAV delay is commenced by declaration of an A-EVENT, and a PAV delay is commenced upon delivery of the A-PACE pulse in certain DDD and DDDR pacing systems.

The A-PACE and V-PACE pulses are produced by the exponential discharge of respective atrial and ventricular output capacitors through the impedance loads in the atrial and ventricular pacing paths that each include a coupling capacitor, the active and indifferent pace/sense electrodes, and the patient's heart tissue between the pace/sense electrodes. In conventional dual chamber pacing systems, both the atrial and ventricular sense amplifiers are "blanked", i.e., uncoupled, from the respective atrial and ventricular pace/sense electrode pairs during the delivery of either of an A-PACE pulse or a V-PACE pulse and for a programmed blanking period thereafter. The gains of the atrial and ventricular sense amplifiers are normally tuned for the relatively low voltages of the heart (e.g., 0.3 mV-4.0 mV for the atrial sense amplifier and 1.0 mV-20.0 mV for the ventricular sense amplifier). The significantly greater voltages of the A-PACE and V-PACE pulses (e.g., varying between 0.5 V and 8.0 V) must be blocked from the atrial and ventricular sense amplifiers.

Moreover, a residual post-pace polarization signal (or "after-potential") remains in the pacing path due to the residual energy in the impedance load that the output capacitor is discharged into to deliver the A-PACE or V-PACE pulse. The impedance load across the output amplifier terminals comprises the impedance of the coupling capacitor, the lead conductor(s), the tissue-electrode interface impedances, and the impedance of the body tissue bulk between the active and indifferent pace/sense electrodes. The impedances of the body tissue and the lead conductor(s) may be modeled as a simple series bulk resistance, leaving the tissue-electrode interfaces and any coupling capacitors as the reactive energy absorbing/discharging elements of the total load. There are typically two tissue-electrode interfaces in a pacing path, one at the active tip electrode, and one at the indifferent ring (or IPG case or "can") electrode. The energy stored in these interfaces and any coupling capacitors dissipates after the pacing pulse through the pacing path impedance load creating the after-potential that can be sensed at each electrode and affect the ability of the sense amplifiers to sense natural or evoked cardiac events. The tip electrode is the primary after-potential storage element in comparison to the case and ring electrodes. An indifferent ring electrode typically stores more energy than does a can electrode due to differences in electrode areas.

Most current pacemaker output circuits incorporate "fast recharge" circuitry for short-circuiting the pacing path and actively dissipating or countering after-potentials during the blanking of the sense amplifier's input terminals to shorten the time that it would otherwise take to dissipate after-potentials. The primary purposes of providing a recharge operation are to ensure that the coupling capacitor(s) is recharged to an insignificant voltage level or equilibrium prior to the delivery of the next pacing pulse through it and to allow the net DC current in the pacing path to settle to zero to facilitate sensing in the same pacing path or using one of the pace/sense electrodes of that pacing path.

Thus, it is conventional to suppress or blank both of the atrial and ventricular sense amplifiers during A-PACE and V-PACE pulses for blanking periods to avoid overloading the sense amplifier. Moreover, the sense amplifiers may abruptly sense a different potential than was present at the time of initial blanking when the blanking period expires and the sense amplifier is reconnected due to the after-potentials and electrode polarization as well as the recharge function. This can produce unwanted oversensing of artifacts resulting in false declarations of A-EVENTs or V-EVENTs. Therefore, the blanking periods in pacemaker IPGs sold by the assignee of this application are nominally set at 30 ms after delivery of an A-PACE or V-PACE, but the blanking periods may be programmed as long as 45 ms in difficult sensing scenarios. There may be additional digital blanking of the sense amplifiers to avoid sensing of evoked response or other pacing artifacts, e.g., for 150 ms to 400 ms after paced events in ICDs. Such blanking periods are characterized as an atrial blanking periods (ABP) including a post atrial pace, atrial blanking period (PAABP or PAAB) and a post ventricular pace, atrial blanking period (PVABP or PVAB) or as a ventricular blanking periods (VBP) including a post atrial pace, ventricular blanking period (PAVBP or PAVB), and a post ventricular pace, ventricular blanking period (PVVBP or PVB).

In addition, a number of sense amplifier refractory periods are timed out on atrial and ventricular sense event signals and generation of A-PACE and V-PACE pulses, whereby "refractory" A-EVENT and V-EVENTs during such refractory periods are selectively ignored or employed in a variety of ways to reset or extend time periods being timed out. Atrial and ventricular refractory periods (ARP and VRP) are commenced upon an A-EVENT or V-EVENT or generation of an A-PACE or V-PACE pulse, respectively. The ARP is typically only employed by itself during atrial demand pacing in the AAI pacing mode. In dual chamber pacing modes, the ARP commenced by the A-EVENT or A-PACE pulse extends through the SAV delay or the PAV delay until a certain time following a V-EVENT terminating the SAV or PAV delay or generation of a V-PACE pulse at the expiration of the SAV or PAV delay. This post-ventricular atrial refractory period (PVARP) is commenced by a V-PACE pulse or V-EVENT based on the understanding that A-EVENTs sensed during its time-out generally reflect a retrograde conduction of the evoked or spontaneous ventricular depolarization wave and therefore are not employed to reset an escape interval and commence an SAV delay. The duration of PVARP may be fixed or vary as a function of sensed atrial rate or pacemaker defined pacing rate, with the result that in many cases relatively long PVARPs are in effect at lower rates. A total ARP (TARP) is defined as the entire duration of the ARP and the PVARP. See, for example, U.S. Pat. No. 6,311,088. Typically the ARP and VRP are set at 300 ms, and the PVARP durations are programmable in the range of 250 ms-400 ms.

The rate-adaptive VDDR, DDIR, and DDDR pacing modes function in the above-described manner but additionally provide rate modulation of a pacing escape interval between a programmable lower rate and an upper rate limit (URL) as a function of a physiologic signal or rate control parameter (RCP) related to the need for cardiac output developed by a physiologic sensor. At times when the intrinsic atrial rate is inappropriately high or low, a variety of "mode switching" schemes for effecting switching between tracking modes and non-tracking modes (and a variety of transitional modes) based on the relationship between the atrial rate and the sensor derived pacing rate have been proposed as exemplified by commonly assigned U.S. Pat. No. 5,144,949.

In order to maximize the useful life of pacing IPGs, it is desirable that the A-PACE and V-PACE pulse energies be programmed to the minimal energies required to evoke a depolarization of the atria and ventricles (i.e., to "capture" the atria and ventricles). The minimum output pulse energy which is required to capture and thus evoke a muscular depolarization within the heart is referred to as the stimulation threshold, and generally varies in accordance with the well known strength-duration curves, wherein the amplitude of a stimulation threshold current pulse and its duration are inversely proportional. One difficulty that arises from use of the blanking and refractory periods relates to the inability to use the sense amplifiers to detect the capture or loss of capture (LOC) of the atria and ventricles.

Therefore, it has been proposed to employ additional sense electrodes and sense amplifiers or differing combinations of pace/sense electrodes or cardioversion/defibrillation electrodes to sense the evoked response to a V-PACE or A-PACE as described in commonly assigned U.S. Pat. Nos. 5,331,966 and 5,683,431. A subcutaneous electrode array (SEA) formed on the surface of the IPG housing is proposed in the '966 patent for sensing the "far field" EGM at a distance from the heart along vectors selected from the electrodes of the SEA. The far field EGM is employed for a variety of reasons as set forth in the above-referenced '966 patent. The '966 patent also describes a number of other sensing schemes in the prior art for sensing the electrical activity of the heart for determining LOC.

U.S. Pat. No. 3,949,758 relates to a threshold-seeking pacemaker with automatically adjusted energy levels for pacing pulses in response to detected LOC, and describes separate sensing and pacing electrodes, which are each utilized in unipolar fashion with a third common electrode having a comparatively larger dimension, to reduce residual polarization problems.

U.S. Pat. No. 3,977,411 discloses a pacemaker having separate sensing and pacing electrodes that are each utilized in unipolar fashion. The sensing electrode comprises a ring electrode having a relatively large surface area (i.e., between 75 to 200 mm$^2$) for improved sensing of cardiac activity (R-waves), and is spaced along the pacing lead approximately 5 to 50 mm from the distally-located tip electrode used for pacing.

U.S. Pat. No. 3,920,024 discloses a pacemaker having a threshold tracking capability that dynamically measures the stimulation threshold by monitoring the presence or absence of an evoked response (R-wave). Various electrode configurations are illustrated in FIGS. 1B and 9A-9F for purposes of sensing the evoked response, including sensing is between an intracardiac electrode and a reference electrode that is spaced some distance away from the heart or sensing between intracardiac electrodes.

U.S. Pat. No. 4,305,396 also relates to a rate-adaptive pacemaker wherein the output energy is automatically varied in response to the detection or non-detection of an evoked response (R-wave) and the detected stimulation threshold. It is stated to be preferred to use the same electrode for both pacing and sensing, such as a unipolar or bipolar system wherein there is at least one electrode located in the ventricle, but suggests that other lead designs may be utilized such that the sensing and pacing electrode are separate.

U.S. Pat. No. 4,387,717 relates to a pacemaker having a separate (i.e., non-pacing) electrode element, implanted near or in direct contact with the cardiac tissue, and positioned relative to the pacing electrodes (i.e., unipolar pacing from "tip" to "can") to provide improved P-wave and R-wave sensing with minimal interference from the pacing electrodes. The "can" functions as an indifferent electrode for sensing in combination with the separate electrode element. The separate sensing electrode is spaced from the pacing electrodes to minimize cross coupling and interference from the pacing stimulus and after-potentials. The separate sensing electrode comprises an extravascular metallic plate having a comparatively large surface area in one embodiment. In another embodiment the separate sensing electrode comprises a cylindrical metal ring mounted on the insulated pacing lead between the pacemaker and the "tip" electrode, and is described as being located along the lead to permit positioning the sensing electrode either within the heart, externally on the heart wall, or in some remote location in the vascular system away from the heart.

U.S. Pat. No. 4,585,004 relates to an implantable cardiac pacing and monitoring system, wherein the pace/sense electrodes are electrically separate from an auxiliary sense electrode system. The auxiliary sense electrode system comprises a transvenous data lead with ring electrodes for sensing located in the right ventricle (approximately 1 cm from the pacing tip electrode for R-wave sensing) and in the right atrium (approximately 13 cm from the tip electrode to be in close proximity with the S-A node), both ring electrodes being used in conjunction with the pacemaker can in unipolar sensing fashion.

U.S. Pat. No. 4,686,988 relates to a dual chamber pacemaker having atrial and ventricular endocardial leads with a separate proximal ring electrode coupled to a P-wave or R-wave sensing EGM amplifier for detecting the atrial or ventricular evoked response to atrial or ventricular stimulation pulses generated and applied to other electrodes on the endocardial lead system. The auxiliary lead system thus resembles the '004 patent.

U.S. Pat. No. 4,549,548 discloses a programmable DDD pacing system in which the selection of pace/sense electrodes is changed during each pacing cycle to optimize the choice of unipolar and bipolar atrial and ventricular operations. U.S. Pat. Nos. 4,759,366 and 4,858,610 relate to evoked response detector circuits that also employ fast recharge in at least one separate sensing electrode in either unipolar or bipolar electrode configurations in either or both the atrium and ventricle. The cardiac pacing systems function as unipolar and bipolar systems at different steps in the operating cycle. In the '610 patent, a separate electrode on the connector block of the IPG can is suggested for use as the reference electrode anode rather than the metal case itself if the case is employed as the reference electrode for the delivery of the stimulation pulse. In the '366 patent, the detected evoked response is used in an algorithm for adjusting the pacing rate.

U.S. Pat. Nos. 4,310,000, 4,729,376, and 4,674,508 also disclose the use of a separate passive sensing reference electrode mounted on the IPG connector block or otherwise insulated from the pacemaker case in order to provide a sensing reference electrode which is not part of the stimulation reference electrode and thus does not have residual after-potentials at its surface following delivery of a stimulation pulse. The aforementioned '000 patent suggests various modifications to the passive sensing reference electrode depicted in its drawings, including the incorporation of more than one passive sensing reference electrode provided on or adjacent to the IPG can, positioned as deemed necessary for best sensing, and connected to one or more sense amplifiers. No specific use of the additional passive sensing reference electrodes is suggested, although the single passive sensing reference electrode is suggested for use with a sense amplifier to detect both capture and spontaneous atrial or ventricular electrical events in a dual chamber pacing system.

Moreover, it has been proposed in the prior art to automatically select among pacing and sensing electrode pairs during the cardiac cycle or in response to a determination that lead impedance is unacceptable (which may arise from a lead fracture or electrode dislodgement or the like). See, for example, U.S. Pat. Nos. 4,958,632, 5,003,975, and 5,755,742 and the above-referenced '548 patent. According to the '548 patent, the selection of unipolar or bipolar mode of operation is based on a determination for monitoring the amplitude of sensed heartbeat signals to determine whether the sensing operation would be performed better in the unipolar or the bipolar mode. This is directed to a determination of heart performance vis-a-vis the leads involved so as to control the selection of unipolar or bipolar sensing.

Thus, considerable effort has been expended in providing systems and methods for overcoming the limitations on sensing imposed by delivery of a pacing pulse across a pair of pace/sense electrodes for a variety of purposes, including detection of LOC and determination of pacing thresholds, determination of lead impedance, and selection of the optimal pacing and sensing electrode pairs. Despite these improvements, pacing systems still employ the above-described atrial and ventricular blanking functions.

Disruption of AV electrical and mechanical synchrony frequently arises due to the spontaneous depolarization of the ventricles triggered at an ectopic site in one of the ventricles. Such a spontaneous ventricular depolarization that is not associated with a prior atrial depolarization is characterized as a premature ventricular contraction (PVC). Many of the problems resulting from the occurrence of a PVC in a patient with a dual chamber pacemaker are described more fully in U.S. Pat. Nos. 4,788,980 and 5,097,832.

PVCs that occur during the V-A interval following a prior detected R-wave or delivery of a V-PACE pulse are usually sensed as V-EVENTs that restart the V-A interval. PVCs that occur during the time-out of the AV delay and following time-out of the PAVBP are indistinguishable from sinus ventricular depolarizations that are conducted from the AV node through the Bundle of His. The resulting V-EVENT inhibits delivery of the V-PACE, and the V-A interval is commenced.

As noted above, after-potentials on the ventricular pace/sense electrodes at time-out of the PAVBP can erroneously be detected and result in declaration of a V-EVENT by the ventricular sense amplifier. The pacing system will not provide appropriate ventricular pacing to a patient's heart having AV block if electrical noise or other signals are mistakenly sensed by the ventricular sense amplifier as V-EVENTS during timeout of the AV delay. The questionable nature and consequences of mistakenly detecting V-EVENTs has led to the adoption of the practice of delivering a ventricular safety pace (VSP) pulse at a fixed time, typically 110 ms, following delivery of an A-PACE. In other words, a VSP pulse is delivered to the ventricular pace/sense electrodes if a V-EVENT is declared between the time-out of the PAVBP and a 110 ms VSP window following delivery of an A-PACE pulse. This 110 ms VSP window is often denoted the cross talk window. The 110 ms VSP window length is shorter than the normal AV conduction time in humans, so any V-EVENT declared within the VSP window is unlikely to be due to true AV conduction. The delivered VSP pulse captures the ventricles if the V-EVENT was due to cross talk, that is, sensing of the residual A-PACE energy afterpotentials. The delivered VSP pulse will not capture the ventricles if the V-EVENT reflects a PVC, because the ventricles will be refractory at that time. Thus, faced with this uncertainty, a VSP pulse is delivered at time-out of the VSP window or delay so as to ensure that the ventricles are truly contracting at a safe time after delivery of the A-PACE pulse. The VSP function is a programmable feature of prior art pacing systems that may be programmed off by the physician if desired. One form of VSP operation is set forth in U.S. Pat. No. 4,825,870, for example.

However, it frequently happens that the depolarization wavefront of a PVC reaches the pace/sense electrodes during the PAVBP, and the ventricular sense amplifier does not detect the R-wave. The after-potentials from the PVC wavefront may not be strong enough at the ventricular pace/sense electrodes to trigger a V-EVENT at time-out of the ventricular blanking period. Thus, a V-PACE pulse may be delivered at the time-out of the AV delay. The AV delay may be programmed to be long enough so that the V-PACE is delivered during the vulnerable period of the ventricles. The vulnerable period occurs during the T-wave repolarization of the ventricle (approx. 250 ms-400 ms). During the vulnerable period, there is a dispersion of refractoriness where some cardiac cells are repolarized while others are still refractory. Additional stimulation during this time has a higher likelihood of initiating a tachyarrhythmia than during periods where the cardiac cells are either completely refractory or completely repolarized.

BRIEF SUMMARY OF THE INVENTION

In accordance with the present invention, AV synchronous, dual chamber pacing systems or any atrial based pacing system requiring ventricular sensing are provided having improved sensing of normal ventricular depolarizations or ectopic ventricular depolarizations coincidentally occurring at or shortly following delivery of an A-PACE pulse. Ventricular activations can occur coincident with an A-PACE pulse or otherwise within the PAVBP in a number of scenarios, such as ectopic ventricular depolarizations, also referred to as premature ventricular contractions (PVCs) and normal ventricular activations during atrial under-sensing or intermittent loss of atrial capture. For convenience and because the most common form of under-sensed ventricular activation is due to PVCs, any such ventricular depolarization occurring coincident with the delivery of an A-PACE pulse is characterized herein as a PVC.

The QRS complex of such a PVC that appears between tightly spaced, near field, ventricular pace/sense electrodes is relatively narrow and exhibits a pronounced R-wave peak that is excellent for ventricular sensing when the ventricular sense amplifier is not blanked. Accordingly, the ventricular sense amplifier is preferably coupled with bipolar pace/sense electrodes and advantageously provides robust sensing of PVCs or conducted R-waves when it is not blanked. However, the narrow QRS complex sensed across the closely spaced ventricular pace/sense electrodes dissipates by the time that the PAVBP times-out as the depolarization wave front propagates through the ventricles and past the ventricular pace/sense electrodes. Therefore, the R-wave peak of a PVC occurring within the PAVBP is not sensed by the ventricular sense amplifier when the PAVBP times-out. A need therefore remains for a capability of sensing such PVCs falling within the PAVBP We have observed that the QRS complexes of such PVCs observed across widely spaced sense electrodes are relatively wide and are less susceptible to under-sensing during the PAVBP. We have also observed that sense electrodes that are spatially separated from the ventricular pace/sense electrodes add additional sensing capabilities because of the propagation delay of the QRS wavefront between such remote electrodes. In accordance with the present invention, a PVC occurring coincident with or shortly following delivery of an A-PACE pulse that would fall within the PAVBP is sensed employing a PVC sense amplifier that is coupled to such widely spaced sense electrodes that do not include both of the ventricular pace/sense electrodes coupled to the ventricular sense amplifier subjected to the PAVBP. The PVC sense amplifier may be blanked simply during delivery of the A-PACE pulse to protect the sense amplifier circuitry from the applied pacing voltage, but can then sense the relatively wide QRS complex of the PVC that persists longer than the A-PACE pulse.

Therefore, in one embodiment of the present invention, a first ventricular sense amplifier is coupled to active and indifferent ventricular pace/sense electrodes for sensing natural ventricular depolarizations and declaring a V-EVENT. The first ventricular sense amplifier is blanked during the PAVBP following delivery of an A-PACE pulse. A far field or unipolar PVC sense amplifier coupled to a far field, PVC sense electrode pair detects such PVCs while the ventricular sense amplifier coupled to the active and indifferent ventricular pace/sense electrodes is blanked. The far field PVC sense electrode pair is disposed in the patient's body to define a far field PVC sense vector differing from a ventricular sense vector defined by the active and indifferent ventricular pace/sense electrodes.

In another aspect of the present invention, the VSP function is advantageously augmented by the redundant sensing capability provided by the first ventricular sense amplifier and the PVC sense amplifier. As described above, when a PVC is under-sensed in a dual chamber pacing system, a V-PACE pulse is delivered at the end of the AV interval. At nominal AV intervals, the ventricle is typically refractory to a subsequent V-PACE pulse. However, a V-PACE pulse delivered after a long AV interval has a greater probability of capturing the heart. The V-PACE pulse may be delivered within a patient's vulnerable period and in certain circumstances may initiate an arrhythmia in a susceptible patient. The mounting evidence suggesting long-term deleterious effects of right ventricular apical pacing may increase physician motivation to extend the AV interval to decrease ventricular pacing. Ventricular safety pacing ensures a ventricular beat for each cardiac cycle and ensures that the V-PACE pulse is not delivered in the ventricular vulnerable period. This is accomplished by delivering the VSP pulse shortly after the A-PACE pulse when a V-EVENT is detected closely following the delivery of the A-PACE pulse. The subsequent VSP pulse will capture the heart if a V-EVENT was declared due to noise, but the subsequent VSP pulse will not capture the heart if the V-EVENT was due to sensing of a PVC. In accordance with this aspect of the present invention, a VSP pulse is delivered if either of the ventricular sense amplifier that is subjected to the PAVBP or the PVC sense amplifier declares a V-EVENT. In this way, the sensing of such PVCs occurring coincident with the delivery of A-PACE pulses is improved and the potential for ventricular pacing during the vulnerable period is minimized.

In the simplest atrial pacing systems, the PVC sense electrode pair can comprise one of the ventricular pace/sense electrodes and an indifferent electrode supported on or comprising the conductive IPG can defining a unipolar PVC sense vector. Or, the PVC sense electrode pair can comprise a selected pair of sense electrodes of an SEA supported by the IPG enclosure defining an optimal PVC sense vector. Or, in an ICD context providing atrial pacing, the PVC sense electrode pair can comprise a further cardioversion/defibrillation electrode pair defining an optimal PVC sense vector or can comprise one of the further cardioversion/defibrillation electrodes and the indifferent electrode supported on or comprising the conductive IPG can defining a optimal PVC sense vector. Or, in a right and left heart pacing context providing atrial pacing, the PVC sense electrode pair can comprise right and left heart chamber pace/sense electrodes defining an optimal PVC sense vector or can comprise one of the left heart chamber pace/sense electrodes and the indifferent electrode supported on or comprising the conductive IPG can defining an optimal PVC sense vector.

Preferably, the far field sense electrode pair can be selected in a test routine or work-up by the physician commenced by programming a PVC sense electrode pair coupled with the PVC sense amplifier and entering a test routine. The results of the test routines of available PVC sense electrode pairs can be compared to identify the optimal PVC sense vector.

As noted above, the ability to detect a PVC during the PAVBP can be employed advantageously to trigger VSP pacing or to inhibit ventricular pacing, which in either case avoids delivery of a V-PACE pulse at the time-out of the PAV delay possibly into the vulnerable period of the heart cycle. The ability to detect a PVC at other times during the PAV or SAV delay or the V-A interval can advantageously be employed to confirm declarations of V-EVENTs, leading to more robust V-EVENT sensing.

Advantageously, the PVC sense amplifier can be enabled during the cardiac cycle, to function as a conventional EGM sense amplifier so that the spontaneously occurring PQRST complexes can be recorded for real time analysis or data storage as is well known in the art.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE INVENTION

In the following detailed description, references are made to illustrative embodiments of methods and apparatus for carrying out the invention. It is understood that other embodiments can be utilized without departing from the scope of the invention.

Figure 1:
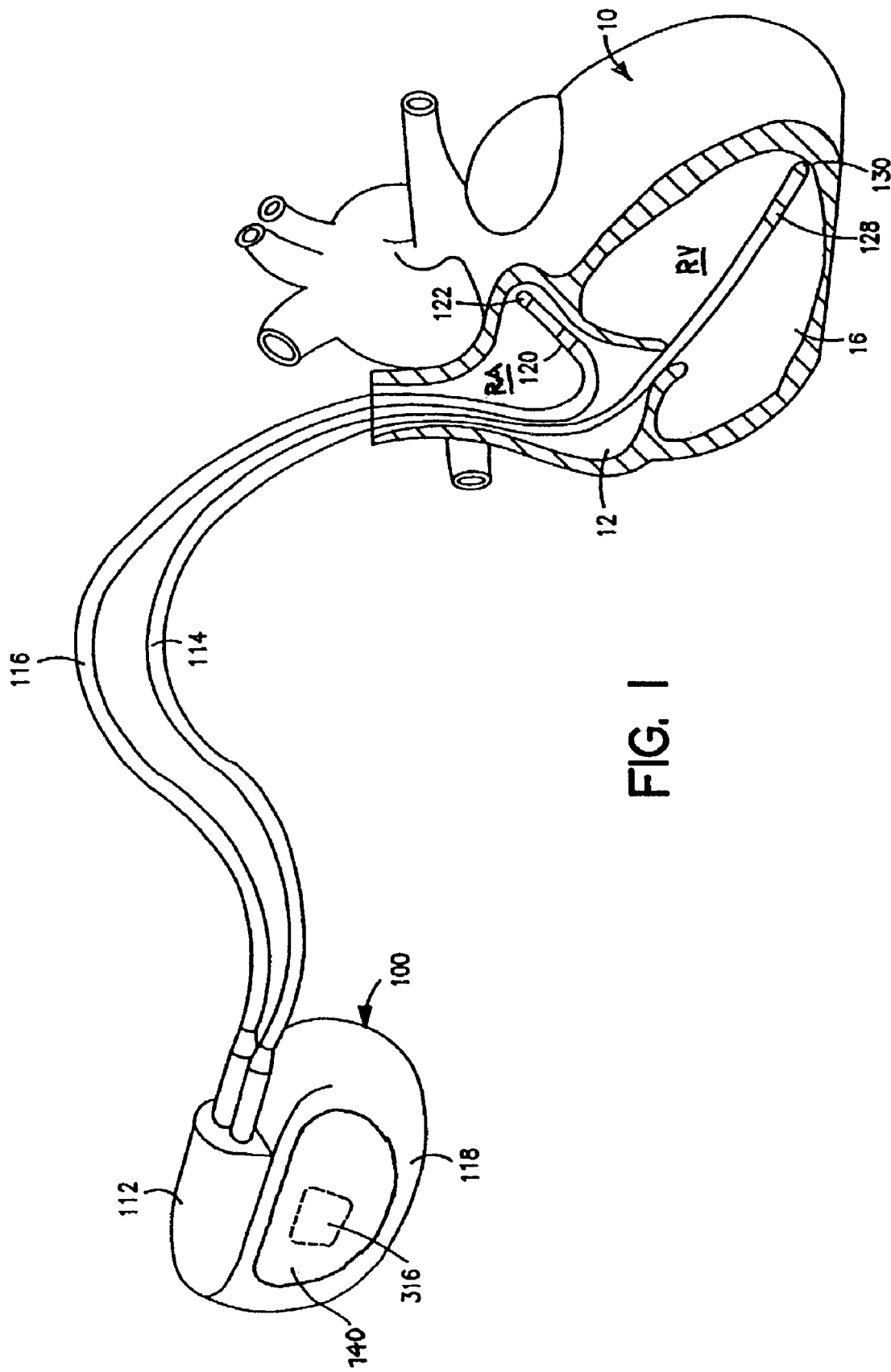
FIG. 1 is a schematic illustration of a dual chamber pacemaker implanted in a patient's chest comprising an IPG and endocardial leads transvenously introduced into the right atrium and right ventricle of the heart, wherein PVC sensing can be conducted during the PAVBP across selected far field sensing electrode pairs.
Figure 2:
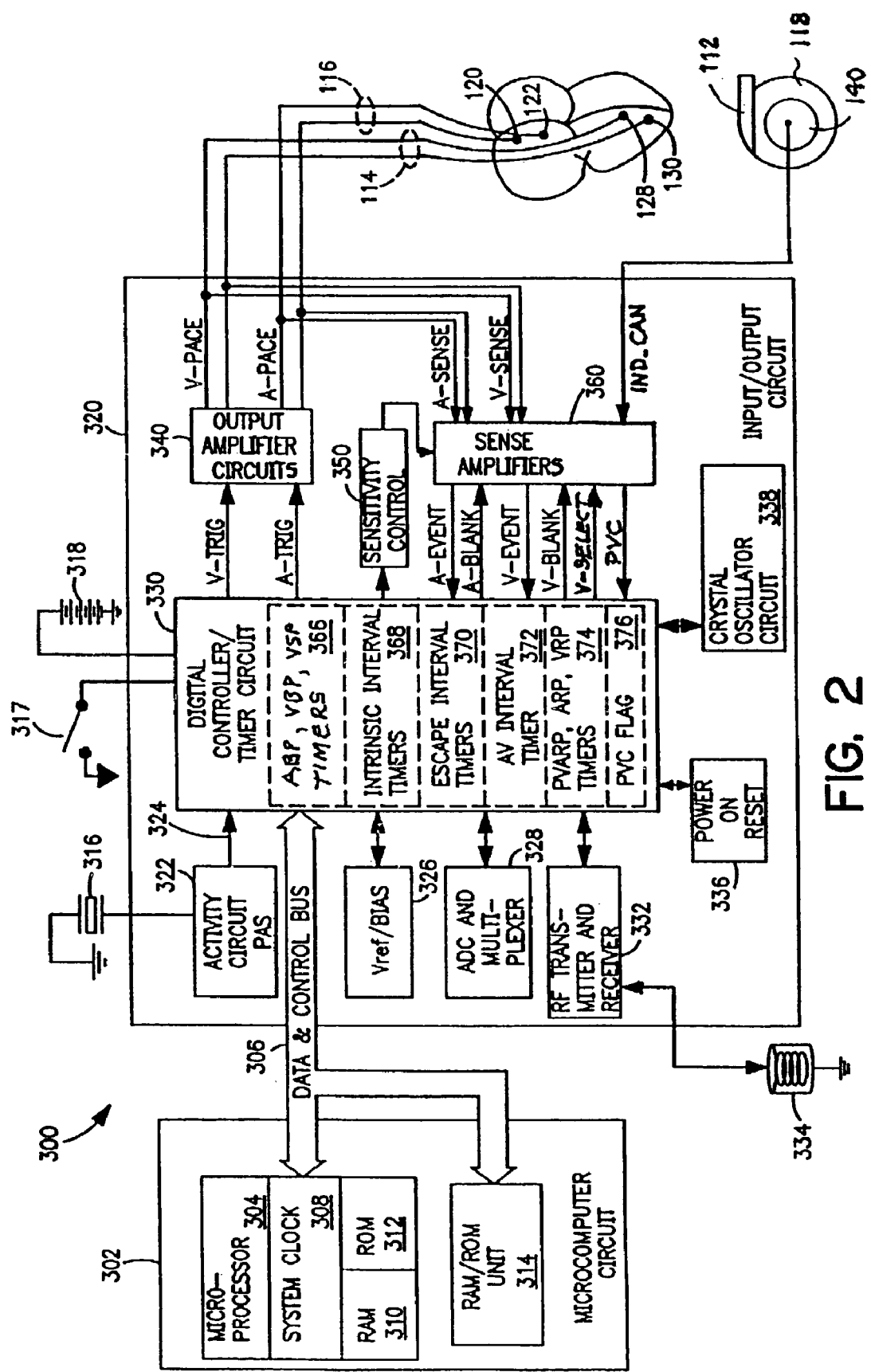
FIG. 2 is a block diagram of the pacing IPG of FIG. 1 in which the present invention may be practiced.

FIGS. 1 and 2 depict the external configuration and components of a typical implantable dual chamber pacemaker operating in a DDD, DDI, DDIR, or DDDR pacing mode or operating in an MI or MIR pacing mode to provide atrial pacing in the absence of an adequate atrial heart rate as long as ventricular sensing indicates normal AV conduction. Such a dual chamber IPG 100 and unipolar or bipolar atrial and ventricular leads 114 and 116 (bipolar leads are depicted), in which the present invention may be implemented is depicted in FIGS. 1 and 2. The dual chamber pacemaker IPG 100 senses and paces in the atrial and ventricular chambers, and pacing is either triggered and inhibited depending upon sensing of intrinsic, non-refractory atrial and ventricular depolarizations during the sequentially timed V-A interval and AV delay, respectively, as is well known in the art, in accordance with the steps set forth in the flow chart of FIG. 3. The present invention functions when the atria are paced due to failure to detect atrial depolarizations or when the sensed atrial heart rate falls below a rate dictated by a RCP related to the need for cardiac output developed by a physiologic sensor.

In addition, the present invention can be implemented in such a dual chamber pacing system that is incorporated into a dual chamber pacing ICD or into a right and left heart pacing system by itself or that is incorporated into a multi-chamber pacing IPG. The following description is thus intended to encompass all of the various types of dual chamber pacemaker systems in which the present invention can be implemented.

The IPG 100 is provided with a hermetically sealed enclosure or can 118, typically fabricated of bio-compatible metal such as titanium, enclosing the dual chamber IPG circuit 300 depicted in FIG. 2. A connector block assembly 112 is mounted to the top of the can 118 to receive electrical connectors located on the proximal connector ends of the depicted bipolar atrial and ventricular pacing leads 114 and 116.

As described further below, an electrically exposed area of the can 118 functions as an IND_CAN electrode 140 that is electrically connected to one input of a PVC sense amplifier to facilitate sensing of PVCs over the heart cycle, particularly to facilitate sensing PVCs during the PAVBP following delivery of an A-PACE pulse.

The bipolar atrial pacing lead 116 extends between its proximal connector coupled to IPG 100 and distal atrial pace/sense electrodes 120 and 122 located in the right atrium 12 of heart 10 to enable sensing of P-waves and delivery of atrial pacing pulses to the right atria. Atrial pacing pulses may be delivered between electrodes 120 and 122 in a bipolar pacing mode or between electrode 122 and the IND_CAN electrode 140 of the IPG 100 in a unipolar pacing mode. Sensing of P-waves by the atrial sense amplifier subject to atrial blanking may occur between electrode 120 and electrode 122 in a bipolar sensing mode or between either of electrode 120 and 122 and the IND_CAN electrode 140 of the IPG 100 in a unipolar atrial sensing mode.

Similarly, the bipolar ventricular pacing lead 114 extends between its proximal connector coupled to IPG 100 and distal ventricular pace/sense electrodes 128 and 130 located in the right ventricle 16 of heart 10 to both sense R-waves and to deliver ventricular pacing pulses to the ventricles. Ventricular pacing pulses may be delivered between electrodes 128 and 130 in a bipolar pacing mode or between electrode 130 and the IND_CAN electrode 140 of the IPG 100 in a unipolar pacing mode. Sensing of R-waves by the ventricular sense amplifier subject to blanking occurs between electrodes 128 and 130 in a bipolar sensing mode in this preferred embodiment.

The IPG circuit 300 within IPG 100 and the bipolar atrial and ventricular leads 114 and 116 are depicted in FIG. 2 in relation to heart 10. The IPG circuit 300 is divided generally into a microcomputer circuit 302 and a pacing input/output circuit 320. The input/output circuit 320 includes the digital controller/timer circuit 330, the atrial and ventricular pacing pulse output circuit 340 and the atrial and ventricular sense amplifiers circuit 360, as well as a number of other components and circuits described below. The digital controller/timer circuit 330 provides control of timing and other functions within the input/output circuit 320. Digital controller/timer circuit 330, operating under the general control of the microcomputer circuit 302, includes a set of timing and associated logic circuits, of which certain ones pertinent to the present invention are depicted and described further below.

Preferably, the IPG 100 or one of the leads 114 or 116 includes one or more physiologic sensor that develops a physiologic signal that relates to the need for cardiac output. The use of physiologic sensors to provide variation of pacing rate in response to sensed physiologic parameters, such as physical activity, oxygen saturation, blood pressure and respiration, has become commonplace.

Commonly assigned U.S. Pat. Nos. 4,428,378 and 4,890,617 disclose activity sensors that are employed to vary the pacing escape interval in single and dual chamber pacemaker IPGs in response to sensed physical activity. Such an activity sensor 316 is coupled to the inside surface of the IPG hermetically sealed enclosure 118 and may take the form of a piezoelectric crystal transducer as is well known in the art. The activity sensor 316 generates an output signal in response to certain patient activities, e.g. ambulating, that is processed and used as a rate control parameter (RCP). If the IPG operating mode is programmed to a rate responsive mode, the patient's activity level developed in the patient activity circuit (PAS) 322 is monitored, and a sensor derived V-A, A-A or V-V escape interval is derived proportionally thereto. A timed interrupt, e.g., every two seconds, may be provided in order to allow the microprocessor 304 to analyze the output of the activity circuit PAS 322 and update the basic V-A (or A-A or V-V) escape interval employed to govern the pacing cycle and to adjust other time intervals as described below.

The bipolar leads 114 and 116 are illustrated schematically with their associated pace/sense electrode sets 120, 122 and 128, 130, respectively, as coupled directly to the atrial and ventricular pacing pulse output circuit 340 and sense amplifiers circuit 360 of pacing circuit 320. The atrial and ventricular pacing pulse output circuit 340 and sense amplifiers circuit 360 contain pulse generators and sense amplifiers corresponding to any of those presently employed in commercially marketed cardiac pacemakers for atrial and ventricular pacing and sensing.

Sense amplifiers circuit 360 also comprises a PVC sense amplifier coupled with the IND_CAN electrode 140 and one of the ventricular pace/sense electrodes 128 or 130 selected by a ventricular select (V-SELECT) signal so that PVCs can be sensed along a bipolar or far-field sense vector. It will be understood that other sense electrodes can be coupled to the PVC sense amplifier within the sense amplifiers circuit 360 and selected by an appropriate V-SELECT signal through programming commands in the course of a telemetry session.

Sensitivity settings of the atrial and ventricular sense amplifiers and the PVC sense amplifier in sense amplifiers circuit 360 can be programmed by the physician to reliably sense true P-waves, R-waves and PVCs during a patient work-up at implantation or during a patient follow-up telemetry session. Digital controller/timer circuit 330 controls the sensitivity settings of the atrial and ventricular sense amplifiers in sense amplifiers circuit 360 by means of sensitivity control 350.

The depicted counters and timers within digital controller/timer circuit 330 include ABP and VBP timers 366, intrinsic interval timers 368 for timing average intrinsic A-A and V-V intervals from A-EVENTs and V-EVENTs, escape interval timers 370 for timing A-A, V-A, and/or V-V pacing escape intervals, an AV delay timer 372 for timing the SAV delay from a preceding A-EVENT or PAV delay from a preceding A-TRIG, refractory period timers 374 for timing ARP, PVARP and VRP times and a PVC flag register 376 that is set upon detection of a PVC. Digital controller/timer circuit 330 starts and times out these intervals and time periods that are calculated by microcomputer circuit 302 for controlling the above-described operations of the atrial and ventricular sense amplifiers in sense amplifiers circuit 360 and the atrial and ventricular pace pulse generators in output amplifier circuit 340.

In order to trigger generation of a V-PACE pulse, digital controller/timer circuit 330 generates a V-TRIG signal at the end of a PAV or SAV delay provided by AV delay timer 372. Similarly, in order to trigger an atrial pacing or A-PACE pulse, digital controller/timer circuit 330 generates an A-TRIG signal at the termination of the V-A interval timed out by escape interval timers 370.

The ABP and VBP timers 366 of digital controller/timer circuit 330 time out the above-described PAVBP and PAABP during and following an A-PACE pulse and the PAVBP and PVVBP during and following a V-PACE pulse. Thus, an atrial blanking (A-BLANK) signal is applied to the atrial sense amplifier for the prevailing ABP, and a ventricular blanking (V-BLANK) signal is applied to the ventricular sense amplifier for the prevailing VBP. In the absence of an A-BLANK signal, atrial depolarizations or P-waves that are detected by the atrial sense amplifier result in an A-EVENT that is communicated to the digital controller/timer circuit 330. Similarly, in the absence of a V-BLANK signal, ventricular depolarizations or R-waves that are detected by the ventricular sense amplifier result in a V-EVENT that is communicated to the digital controller/timer circuit 330. In accordance with the present invention, the PVC sense amplifier within sense amplifiers circuit 360 is only blanked during delivery of the A-PACE pulse to prevent the delivered A-PACE pulse from either damaging the sense amplifier circuitry or being incorrectly sensed as a PVC.

The refractory period timers 374 time the ARP from an A-TRIG pulse or A-EVENT during which a sensed A-EVENT is ignored for the purpose of resetting the V-A interval. The ARP extends from the beginning of the SAV or PAV interval following either an A-EVENT or an A-TRIG and until a predetermined time following a V-EVENT or a V-TRIG. The refractory period timers 374 also time the PVARP from a V-TRIG pulse or V-EVENT during which a sensed A-EVENT is also ignored for the purpose of resetting the V-A interval. The VRP is also timed out by the refractory period timers 374 after a V-EVENT or V-TRIG signal so that a subsequent, closely following V-EVENT is ignored for the purpose of restarting the V-A interval and setting the PVC flag in register 366.

The base ARP, PVARP and VRP that prevails at the lower rate of 60-70 bpm, for example, are either default or programmed parameter values stored in the microcomputer 302. These refractory period parameter values can be fixed for the full operating range of pacing rates between the programmed lower rate and the URL, which may be 120 bpm, for example, or they can be programmed to follow the algorithm for automatically shortening in duration as the paced or intrinsic heart rate increases to ensure that the long refractory periods during the diminishing escape intervals do not prevent delivery of ventricular pacing pulses synchronized to valid intrinsic P-waves.

The A-EVENT is characterized as a refractory A-EVENT if it occurs during time-out of an ARP or a PVARP or a non-refractory A-EVENT if it occurs after time-out of these atrial refractory periods. Similarly, a V-EVENT is characterized as a refractory V-EVENT if it occurs during time-out of a VRP or a non-refractory V-EVENT if it occurs after time-out of the ventricular refractory period. Refractory A-EVENTs and V-EVENTs are typically ignored for purposes of resetting timed out AV delays and V-A intervals, although diagnostic data may be accumulated related to their occurrences.

Microcomputer 302 contains a microprocessor 304 and associated system clock 308 and on-processor RAM and ROM chips 310 and 312, respectively. In addition, microcomputer 302 includes a separate RAM/ROM chip 314 to provide firmware and additional RAM memory capacity. Microprocessor 304 is interrupt driven, operating in a reduced power consumption mode normally, and awakened in response to defined interrupt events, which may include the A-TRIG, V-TRIG, A-EVENT and V-EVENTs.

Microcomputer 302 controls the operational functions of digital controller/timer 324, specifying which timing intervals are employed in a programmed pacing mode via data and control bus 306. The specific values of the intervals timed by the digital controller/timer circuit 330 are controlled by the microcomputer circuit 302 by means of data and control bus 306 from programmed-in parameter values. The microcomputer 302 also calculates the RCP derived or intrinsic atrial rate derived V-V, A-A or V-A interval, the variable AV delay, and the variable ARP, PVARP and VRP. Typically, the AV delay in modern VDD, VDDR, DDD and DDDR pacemakers is either fixed or varies with the prevailing intrinsic atrial rate, measured as an A-A interval, and/or varies as a function of a physiologic sensor derived pacing rate.

Digital controller/timer circuit 330 also interfaces with other circuits of the input output circuit 320 or other components of IPG circuit 300. Crystal oscillator circuit 338 provides the basic timing clock and battery 318 provides power for the pacing circuit 320 and the microcomputer circuit 302. Power-on-reset circuit 336 responds to initial connection of the circuit to the battery 318 for defining an initial operating condition and similarly, resets the operative state of the IPG circuit 300 in response to detection of a low battery condition. Reference mode circuit 326 generates stable voltage reference and currents for the analog circuits within the pacing circuit 320. ADC (analog to digital converter) and multiplexer circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

Data transmission to and from an external programmer (not shown) during a telemetry session is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Reed switch 317 when closed by application of a magnetic field may be employed to enable programming of the pacemaker and also may be employed to convert the pacemaker temporarily to an asynchronous pacing mode such as DOO or VOO. Operation in the asynchronous mode may continue as long as the magnetic field is present, may continue until overridden by the programmer or may continue for a pre-set time period.

The illustrated IPG circuit 300 of FIG. 2 is merely exemplary, and corresponds to the general functional organization of most multi-programmable microprocessor controlled DDD and DDDR cardiac pacemaker IPGs presently commercially available. It is believed that the present invention can readily be practiced using the basic hardware and software of existing microprocessor controlled, dual chamber pacing systems that are incorporated into dual chamber pacemakers or into ICDs or into right and left heart pacing systems. The invention is preferably implemented into the exemplary pacing system by means of modifications to the hardware incorporating the PVC sense amplifier to detect signals across a PVC sense vector during the PAVBP and at other times during the pacing cycle and to declare a PVC if the signal (regardless of its true source) satisfies PVC detection criterion. In addition, software stored in the ROM 310 of the microcomputer circuit 302 responding to such detected PVCs is modified as described further below. However, the operating functions of the present invention may also be usefully practiced by means of a full custom integrated circuit, for example, a circuit taking the form of a state machine, in which a state counter serves to control an arithmetic logic unit to perform calculations according to a prescribed sequence of counter controlled steps.

Figure 3:
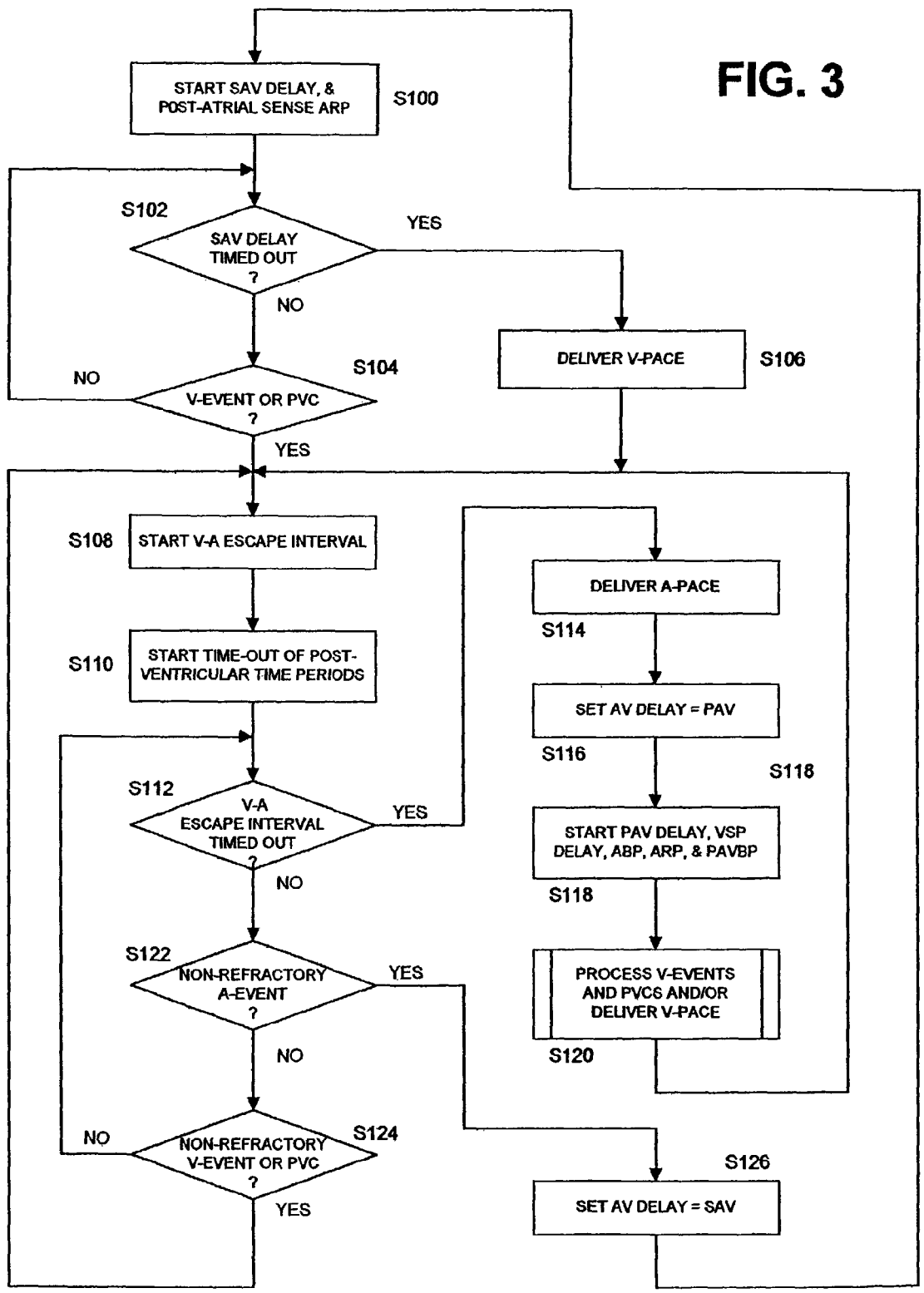
FIG. 3 is flow chart depicting the steps of a DDD pacing cycle.

FIG. 3 is a functional flow chart of the overall pacing cycle timing operation of the pacemaker IPG circuit 300 illustrated in FIG. 2 in the DDD or DDDR pacing modes. In the flow chart of FIG. 3, it is assumed that the A-A or V-V escape interval, cardiac cycle timing of the IPG circuit 300 ranges between a programmed lower rate and a programmed URL and is based on the definition of a V-A interval and an AV delay, specifically either the SAV or the PAV delay interval. The AV delay and V-A interval of any given pacing cycle may be determined as a function of a sensor-derived V-A interval or an atrial rate based V-A interval determined by the average measured intrinsic A-A atrial rate if it is stable and varies between the programmed lower rate and URL. In this particular embodiment, separate SAV and PAV delays are defined, although in practice they may have the same duration. The operations of the flow chart may also incorporate any of the mode switching and sinus preference algorithms of the prior art described above to switch between the use of the sensor or the atrial rate derived escape intervals. However the algorithm is specifically implemented, it is understood to incorporate the PVC response algorithm of the present invention as described hereafter.

For convenience, the pacing cycle is assumed to begin at step S100 starting from a non-refractory A-EVENT. Timing of the prevailing SAV delay and ARP are commenced in step S100, and the system awaits either time out of the SAV delay in step S102 or a non-refractory V-EVENT in step S104. Neither of the atrial and ventricular sense amplifiers is blanked, and the PVC sense amplifier may also be enabled. A V-TRIG and the associated A-BLANK and V-BLANK signals are generated at step S106 at the end of the SAV delay if a non-refractory V-EVENT does not occur at step S104 prior to SAV time-out in step S102.

The SAV delay is terminated without delivery of a V-PACE pulse if either of a PVC or a V-EVENT is declared or if both a PVC and a V-EVENT are declared in step S124, and the V-A interval is restarted in step S108. The redundant sensing of PVCs or other signals by the PVC sense amplifier and the near field R-wave sense amplifier during time-out of the SAV delay provides a robust sensing capability that increases confidence that unnecessary pacing of the ventricles is avoided.

The V-A interval time-out is commenced in step S108, and time-out of the post ventricular time periods including the VRP, PVARP, PAVBP and PVVBP are commenced in step S110. The algorithm awaits expiration of the V-A interval at step S112, and it is possible that a refractory or non-refractory A-EVENT or V-EVENT can occur during the V-A interval time-out.

If a non-refractory A-EVENT is sensed in step S120 during time-out the V-A interval, the V-A interval is terminated, the AV delay is set to the SAV delay in step S124, and the SAV delay and associated post atrial sense ARP is timed out in step S100. Optionally, the non-refractory A-EVENT also causes the V-A interval to be measured by intrinsic interval timer 368 and employed to derive or update the intrinsic atrial rate that is saved in RAM. The V-A interval, the SAV and PAV delays, the PVARP, and the pacing escape interval for the next cardiac cycle can then be recalculated in dependence upon either the updated average A-A interval or upon the RCP in a manner well known in the art.

In the absence of detection of a preceding A-EVENT, if a non-refractory V-EVENT is declared sensed by the near field or bipolar ventricular sense amplifier at step S122 during time out of the V-A interval, then the declared V-EVENT is characterized as a PVC in step S124. It should be noted that such a declaration of a V-EVENT during the V-A interval can be confirmed by the declaration of a PVC by the PVC sense amplifier. Certain algorithms, e.g., those disclosed in the above-referenced '088 patent, have been devised to deal with such PVCs occurring during the V-A interval that could be practiced along with but are not necessary to the practice of the present invention.

An A-TRIG signal is generated in step S114 at the time-out of the V-A interval if the V-A interval times out without sensing any such intervening non-refractory A-EVENT or V-EVENT. In this case, the next succeeding AV delay is defined to be equal to PAV at step S116, and the PAV is timed out in step S118 along with the associated VSP delay and the ARP, ABP and PAVBP in accordance with the steps of FIG. 4. The particular algorithm of FIG. 4 assumes that a VSP function is provided and that the VSP delay is timed out in timers 366 whenever a V-PACE is delivered, but the present invention can be practiced without the VSP function being present or programmed on in a particular case. Moreover, the algorithm of FIG. 4 assumes that the PVC sense amplifier is always enabled, but the PVC sense amplifier could be blanked or disabled during delivery of the A-PACE pulse and V-PACE pulse.

The time-out of the PAV delay is monitored in step S128, and a V-PACE pulse is delivered in step S138 if the PAV delay does time-out without declaration of either of a PVC or a V-EVENT. In step S130, a PVC can be declared at any time during the PAV delay and a V-EVENT can be declared following the time-out of the PAVBP. If the VSP function is not present or programmed ON as determined in step S132, then such a declared PVC or V-EVENT would simply cause the V-A interval to commence in step S108.

However, preferably the VSP function is employed as determined in step S132, and a declared PVC or V-EVENT causes the V-A interval to commence in step S108 only if it is declared after time-out of the VSP delay. If a PVC or V-EVENT is declared in step S130 before time-out of the VSP delay, then a V-PACE is delivered in step S140 at time-out of the VSP delay.

To enable this function, a VSP flag is set in step S136 if a PVC or V-EVENT is declared in step S130 before time-out of the VSP delay as determined in step S134. The status of the VSP flag is checked in step S138 when the VSP delay does time-out as determined in step S134. Since the VSP flag was set in this instance in step S136, then the V-PACE pulse is delivered at time-out of the VSP delay. In this way, a PVC that would otherwise not be detected during the PAVBP does trigger the VSP function to pace the ventricles within a safe time from the PVC and not within the vulnerable period of the heart.

If a PVC or V-EVENT is declared in step S130 after time-out of the VSP delay, as determined in step S134, then a V-PACE is not delivered in step S140. The time-out of the PAV delay is terminated, and the V-A interval is started in step S108. The redundant sensing of PVCs or other signals by the PVC sense amplifier and the near field R-wave sense amplifier in the time period between the end of the VSP delay and the time-out of the PAV delay provides a robust sensing capability that increases confidence that unnecessary pacing of the ventricles is avoided.

The PVC sense amplifier of the depicted embodiment of FIGS. 1 and 2 senses the far field R-wave to particularly detect PVCs across the sensing vector comprising the IND_CAN electrode 10 and one of the ring and tip ventricular pace/sense electrodes 128 and 130. It is expected that the PVC sense amplifier could be advantageously coupled to the IND_CAN electrode 10 and the ring pace/sense electrode 128 because it may not be in the blood and not in contact with endocardial surface resulting in a wide QRS complex. It will be understood from the following that other far field sensing vectors can be selected depending on the available sensing electrodes of the pacing or cardioversion/defibrillation system. The PVC sense amplifier sensitivity can be programmed in a telemetry session to sense intrinsic R-waves appearing in a conventional ECG display. The PVC sense amplifier's uplink telemetered response (the presence or absence of a PVC output signal) can be observed simultaneously. The PVC sense amplifier sensitivity can be varied for each programmed PVC sense vector, and the PVC sense vector providing the best consistent detection of R-waves can be determined. A "permanent" V-SELECT can then be programmed for coupling the PVC sense amplifier inputs to receive the optimal pair of signals across the PVC sense electrodes during chronic implantation.

Figure 4:
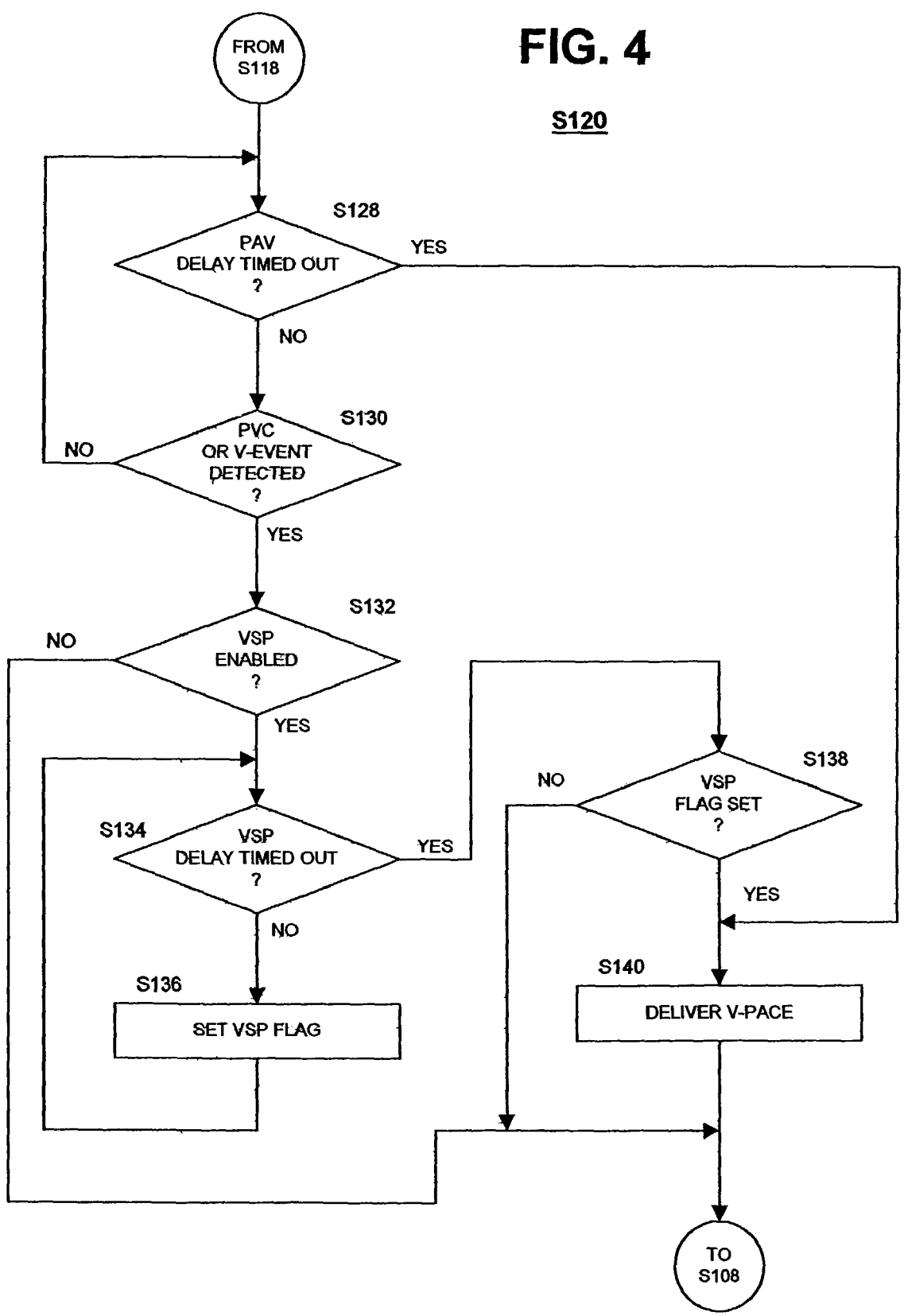
FIG. 4 is a detailed flow chart depicting the steps of detecting and responding to a PVC sensed during the time-out of the PAVBP.
Figure 5:
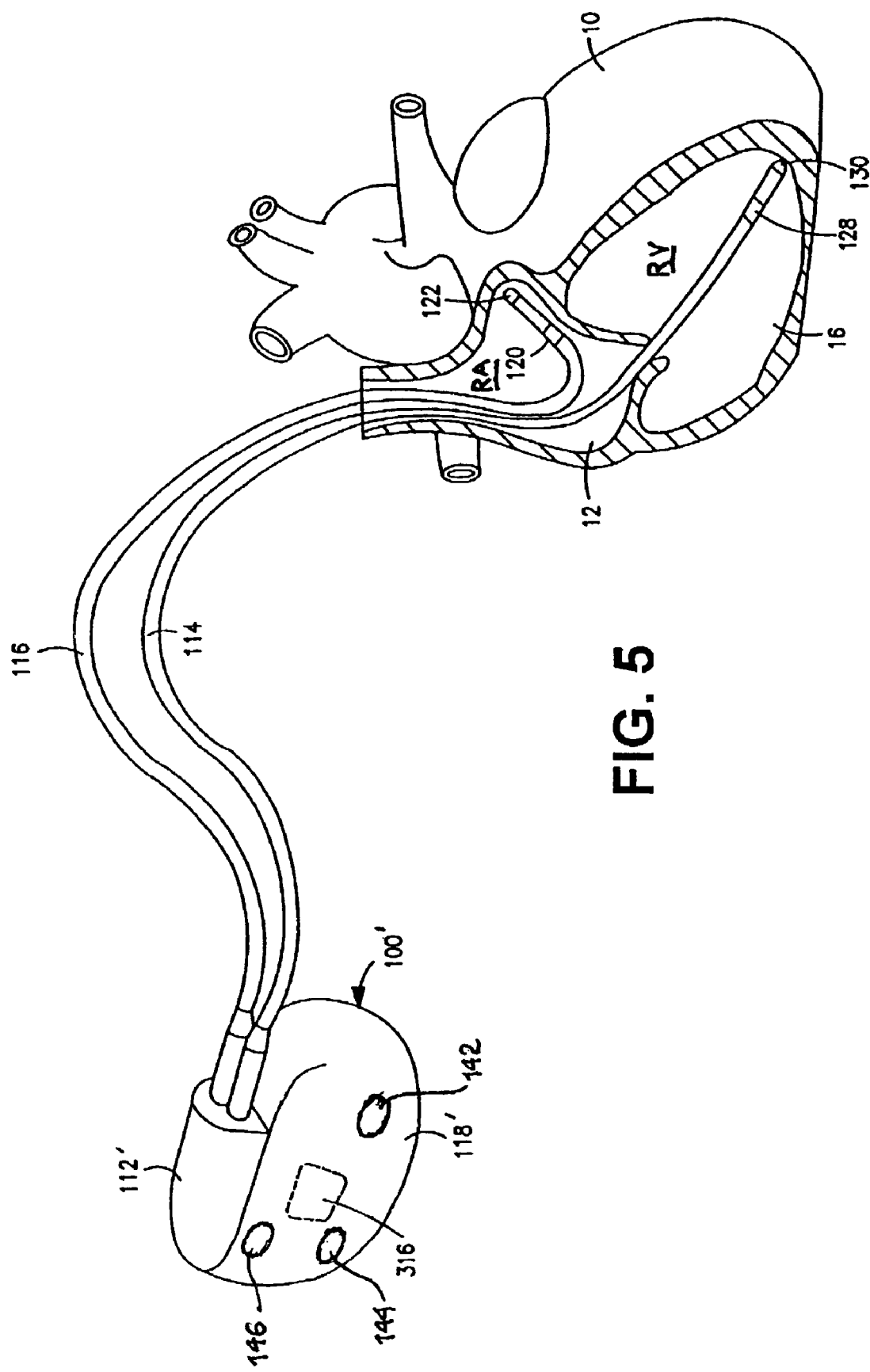
FIG. 5 is a schematic illustration of a further embodiment of a dual chamber pacemaker implanted in a patient's chest comprising an IPG supporting a SEA and endocardial leads transvenously introduced into the right atrium and right ventricle of the heart, wherein PVC sensing can be conducted during the PAVBP across selected far field SEA sense electrode pairs.
Figure 6:
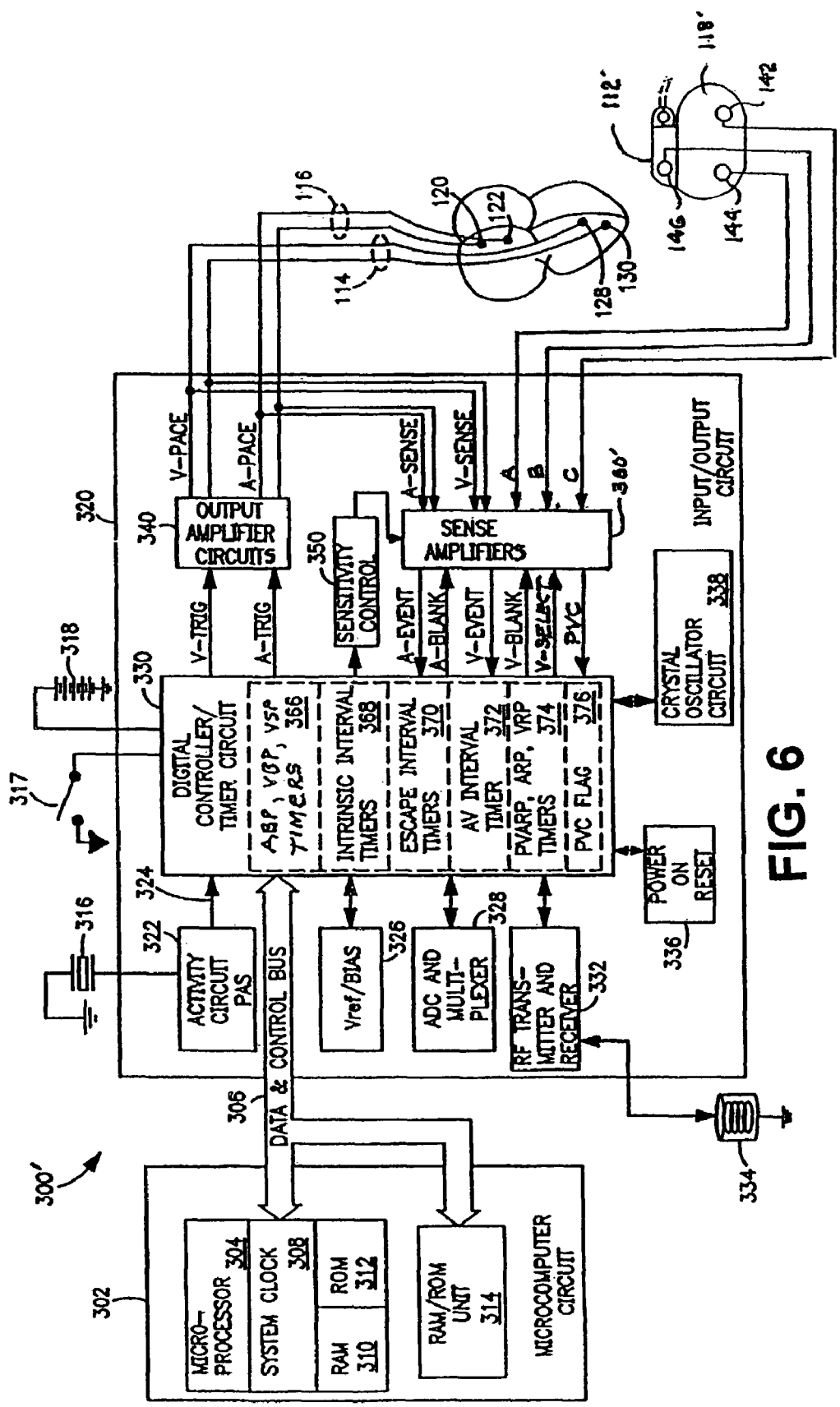
FIG. 6 is a block diagram of the pacing IPG of FIG. 5 in which the present invention may be practiced.

The present invention including the steps of FIGS. 3 and 4, can be practiced in a dual chamber pacemaker of the type depicted in FIGS. 5 and 6 comprising an IPG 100' supporting a SEA on the IPG housing comprising at least one pair of sense electrodes whereby a sense vector or sense vectors can be defined between the sense electrodes. The IPG 100' and IPG circuit 300' conform in most ways to the IPG 100 and IPG circuit 300 described above in reference to FIGS. 1 and 2 with the addition of the SEA. Preferably, the SEA comprises at least three or four orthogonally disposed sense electrodes or more than four sense electrodes disposed around the IPG housing including the IPG connector block and the hermetically sealed enclosure. In the depicted example, the SEA comprises sense electrodes 142, 144, and 146 with sense electrode 146 disposed either on the IPG connector block 112' or the IPG hermetically sealed housing 118'. As in the embodiment of FIGS. 1 and 2, endocardial leads 114 and 116 transvenously introduced into the right atrium 12 and right ventricle 16 of the heart 10. The IPG circuit 300' can select the optimal sensing vector sensed by the PVC sense amplifier within a sense amplifiers circuit 360' by an appropriate V-SELECT command operating additional PVC sense amplifier input switching circuitry of the type disclosed in the above-referenced '966 patent.

The sense electrodes 142, 144, and 146 or the SEA are situated on the IPG housing comprising the connector block 112' and/or the hermetically sealed enclosure 118'. Thus, at least four sense vectors are characterized as far field sense vectors because the SEA is located subcutaneously remote from the heart 10. The SEA provides three or four far field PVC sense vectors comprising PVC sense vector A-B between sense electrodes 146 and 144, PVC sense vector B-C between sense electrodes 144 and 142, and PVC sense vector A-C between sense electrodes 142 and 146 by appropriately coupling the input signals A, B, and C to the PVC sense amplifier inputs within sense amplifiers circuit 360'. A fourth PVC sense vector B-(C-A) can be mathematically derived from the input signals A, B and C, but the simpler selection of a pair of input signals among signals A, B, and C may well suffice in practice and will be assumed in the following description.

The optimal far field sense vector for sensing an R-wave, and, by logical extension, for sensing PVCs occurring during the PAVBP can be determined following implantation of the IPG 100' and the leads 114 and 116 in the patient's body. The sensitivity of the PVC sense amplifier and the V-SELECT pairing signals A, B, and C can both be temporarily programmed in a telemetry session with an external programmer, and the IPG 100' can be commanded to uplink telemeter the PVC sense signal. The intrinsic R-waves and any spontaneously occurring PVCs appearing in a conventional ECG display and the PVC sense amplifier's uplink telemetered response can be observed simultaneously. The PVC sense amplifier sensitivity can be varied for each programmed far field sense vector, and the sense vector providing the best consistent detection of R-waves with the best ventricular sense safety margin can be determined. Other comparative tests to determine the optimal PVC sense vector could include simply measuring the R wave amplitude, the R wave width, and slew rates through the PVC sense amplifier and determining the optimal PVC sense amplifier through comparison of one or a combination of these parameters of the sensed R-waves. Or comparative testing can be conducted varying a blanking period applied to the PVC sense amplifier to determine the PVC sense vector across which an R-wave can be sensed at the longest blanking period. A "permanent" V-SELECT can then be programmed for coupling the PVC sense amplifier inputs to receive the optimal pair of signals A, B, C during chronic implantation.

The chronic operation of the selected far field PVC sense vector can be determined in a telemetry session initiated at a later time from data accumulated in memory registers indicating the number of times that a PVC was detected during the PAVBP and the delivery of a V-PACE was inhibited at time-out of the PAV delay. In IPGs having the VSP function, the saved data would comprise the number of times that a PVC was detected during the PAVBP and/or before time-out of the VSP delay, and the delivery of a V-PACE pulse at time-out of the VSP delay.

In a similar way, optimal PVC sense vectors can be selected in a dual chamber pacing systems providing right and left heart chamber pacing and sensing of the type described in commonly assigned U.S. Pat. No. 6,477,415. Such multi-chamber pacing systems provide right and left atrial and/or ventricular pacing and sensing particularly to enhance cardiac output of hearts in heart failure. In such a right and left heart pacing context providing atrial pacing, the PVC sense electrode pair can comprise right and left heart chamber pace/sense electrodes defining an optimal R-wave sense vector or can additionally comprise one of the left heart chamber pace/sense electrodes and the indifferent electrode supported on or comprising the conductive IPG can defining an optimal PVC sense vector.

Figure 7:
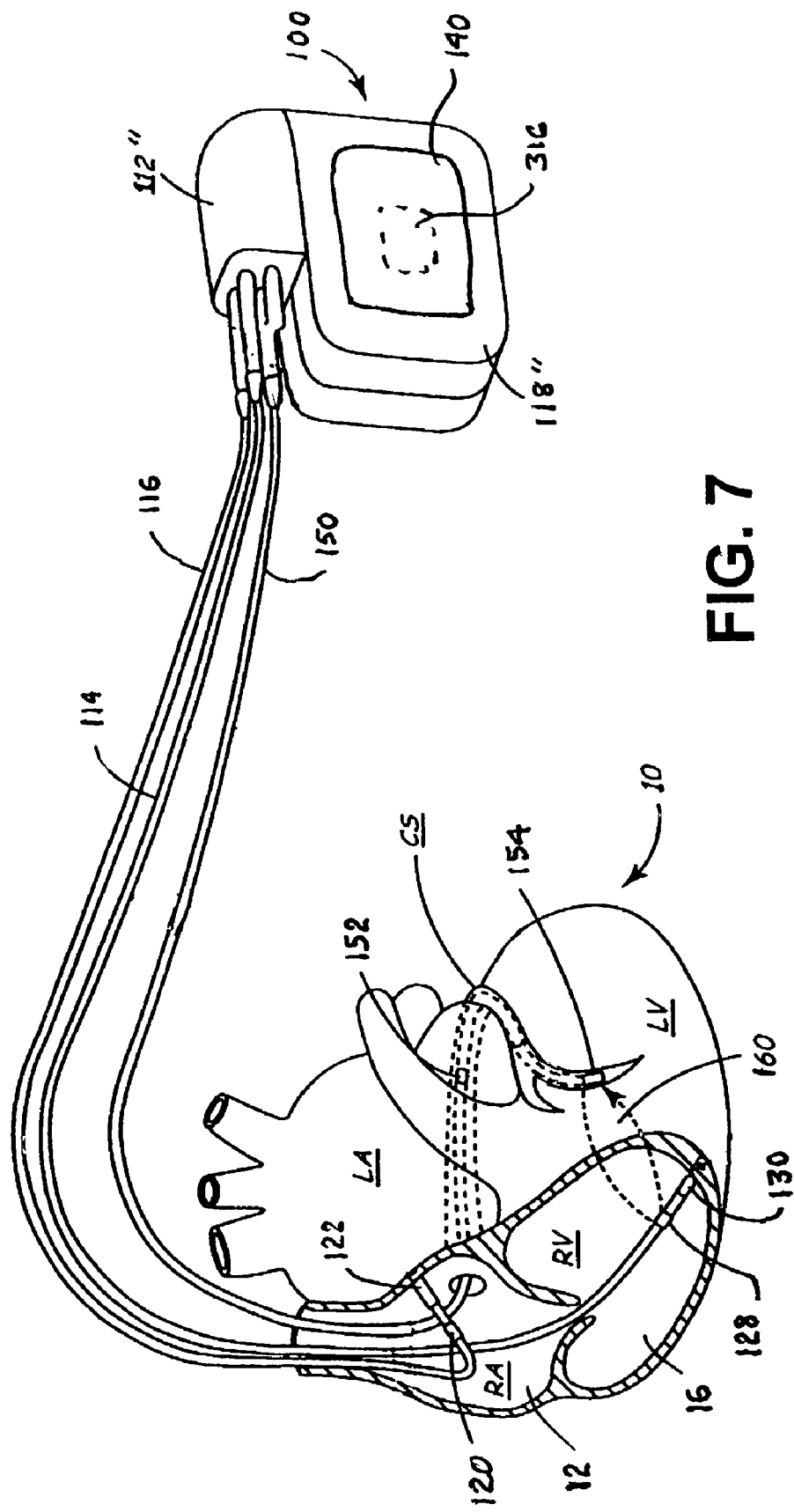
FIG. 7 is a schematic illustration of a further embodiment of a dual chamber, right and left heart pacemaker implanted in a patient's chest and endocardial leads transvenously introduced into the right atrium, right ventricle and coronary sinus of the heart, wherein PVC sensing can be conducted during the PAVBP across selected right and left heart sense electrode pairs.
Figure 8:
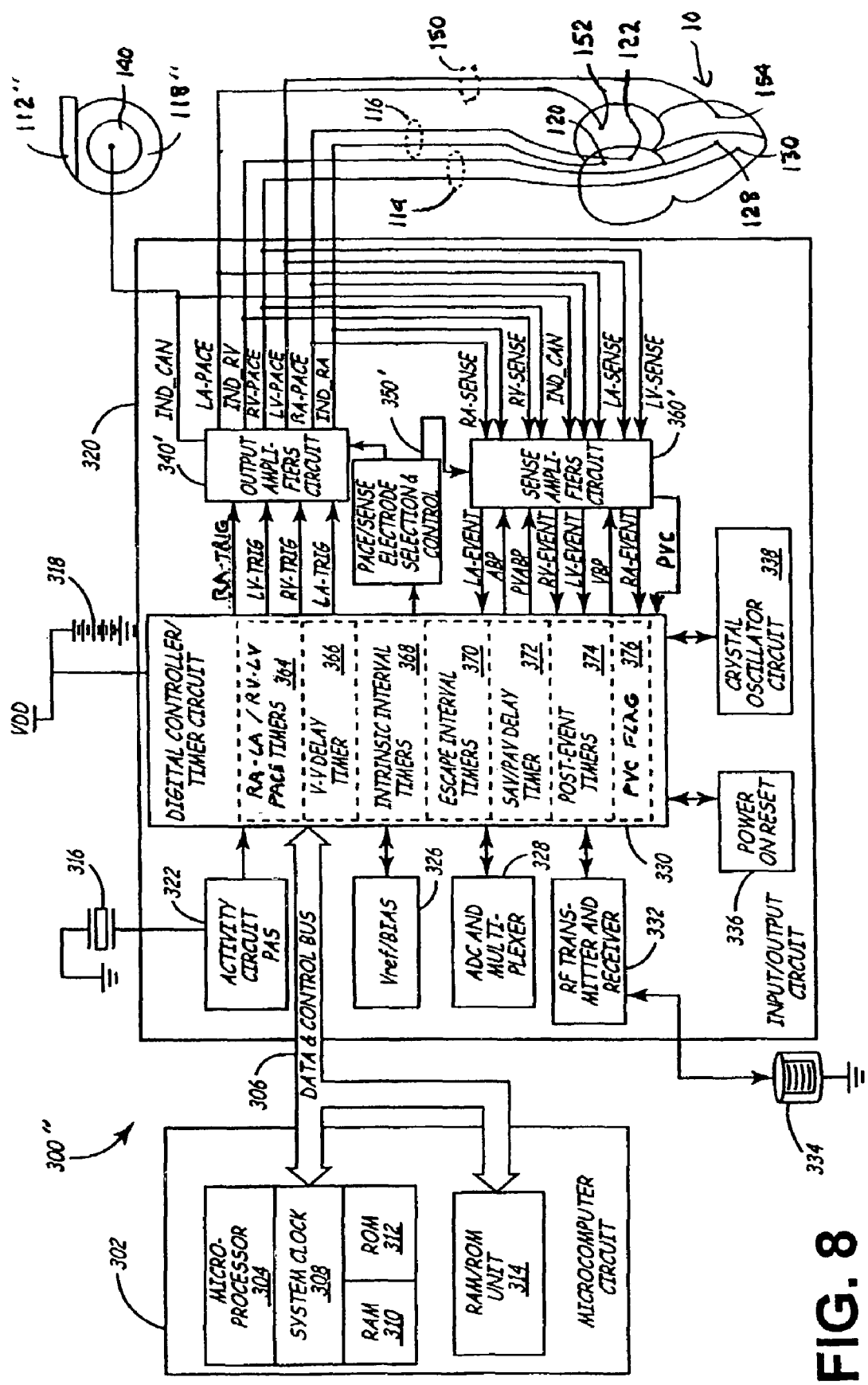
FIG. 8 is a block diagram of the pacing IPG of FIG. 7 in which the present invention may be practiced.

Such a right and left heart pacing system comprising endocardial RV lead 114, RA lead 116, and a CS lead 150 transvenously introduced into the right ventricle 16, the right atrium 12, and the coronary sinus, respectively of the heart 10 and coupled to the connector block 112" of the IPG 100''' is depicted in FIGS. 7 and 8. The depicted CS lead 150 supports an LV pace/sense electrode 154 disposed in the CS or a coronary vein descending from the CS in operative relation to the LV and an LA pace/sense electrode 152 disposed in the CS in operative relation to the LA.

Pacing and sensing in the RA and RV one or both of the LA and LV can be conducted in the manner described in the above-referenced '415 patent. The components of the IPG circuit 300''' correspond in large part with the components of the IPG circuit 300 described above. The flow charts of FIGS. 3 and 4 are followed, and right and left heart pacing pulses can be delivered simultaneously or with a delay as determined in block 364 of digital controller/timer circuit 330. The output amplifiers circuit 340' can deliver the depicted RA-PACE, LA-PACE, RA-PACE and RV-PACE pulses through selected pace/sense electrode pairs or employing the can electrode 140 as an indifferent pacing electrode.

Similarly, the sense amplifiers circuit 360' includes the respective atrial and ventricular sense amplifiers for declaring an LA-EVENT, an RA-EVENT, an LV-EVENT or an RV-EVENT through selected pace/sense electrode pairs or employing the can electrode 140 as an indifferent sense electrode.

A PVC sense vector can be defined by an appropriate V-SELECT command through pace/sense electrode selection and control circuit or registers 350'. In this embodiment illustrated in FIGS. 7 and 8, the PVC sense vector can be selected by an appropriate V-SELECT command among: (1) the can electrode 140 and the RV ring pace/sense electrode 128; (2) the can electrode 140 and the LV pace/sense electrode 154; (3) the LA pace/sense electrode 152 and the LV pace/sense electrode 154; (4) the LA pace/sense electrode 152 and the RV ring pace/sense electrode 128; and (5) the RV ring pace/sense electrode 128 the LV pace/sense electrode 154 depicted as PVC sense vector 160 in FIG. 7. The selection can be made employing comparative testing of the PVC sense electrode pairs as described above.

In a similar way, PVC sense vectors can be selected in a dual chamber pacing ICD implanted in a patient's chest comprising an ICD IPG and endocardial leads transvenously introduced into the right atrium, right ventricle, and coronary sinus of the heart bearing pace/sense and/or cardioversion/defibrillation electrodes, wherein PVC sensing can be conducted during the PVAB period across selected far field PVC sense electrode pairs. The dual chamber ICD can also be configured to provide right and left heart pacing and/or have at least one SEA electrode provided.

Figure 9:
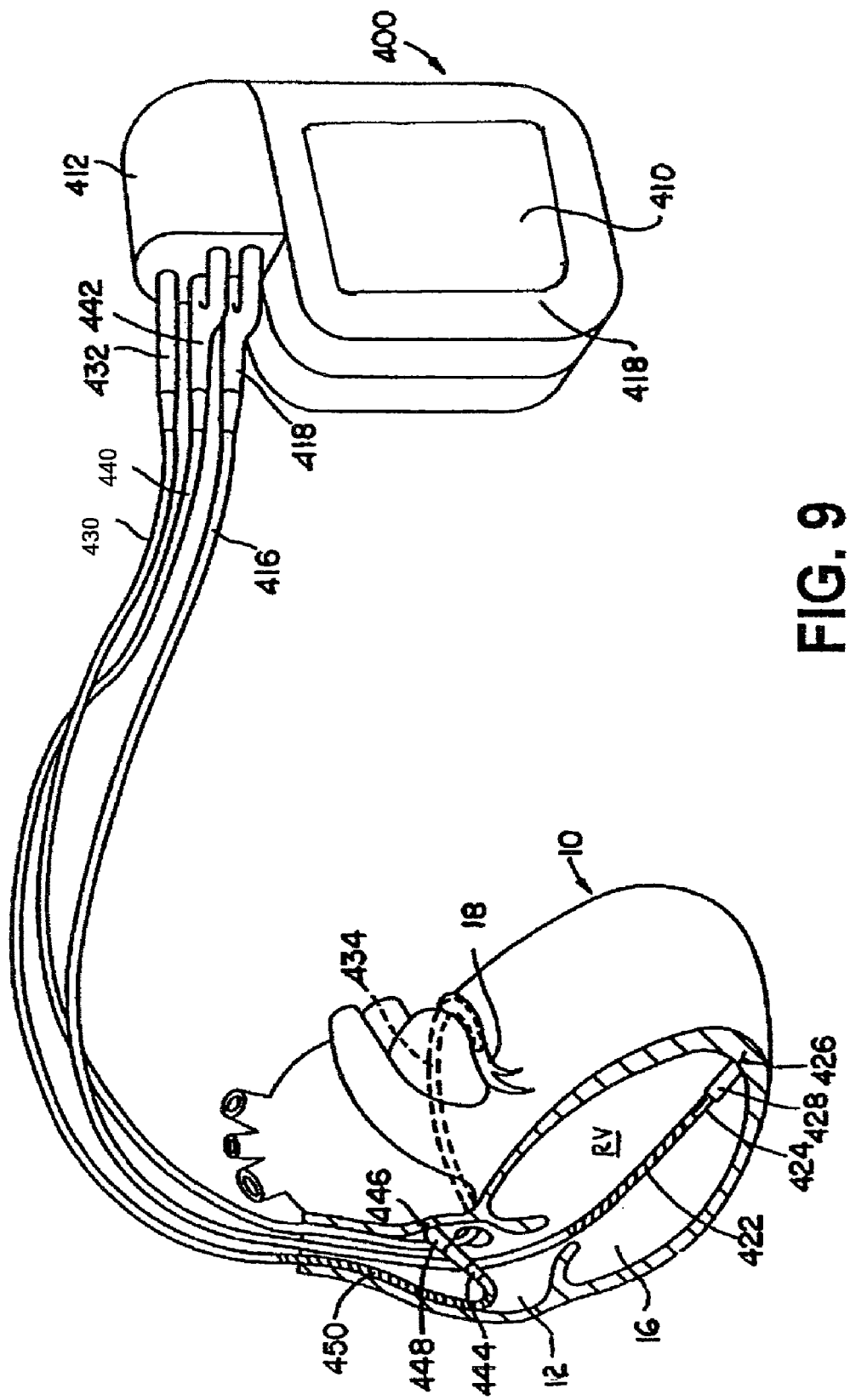
FIG. 9 is a schematic illustration of a dual chamber pacing ICD implanted in a patient's chest comprising an IPG and endocardial leads transvenously introduced into the right atrium, right ventricle, and coronary sinus of the heart supporting pace/sense and/or cardioversion/defibrillation electrodes, wherein PVC sensing can be conducted during the PAVBP across selected far field sensing electrode pairs.
Figure 10:
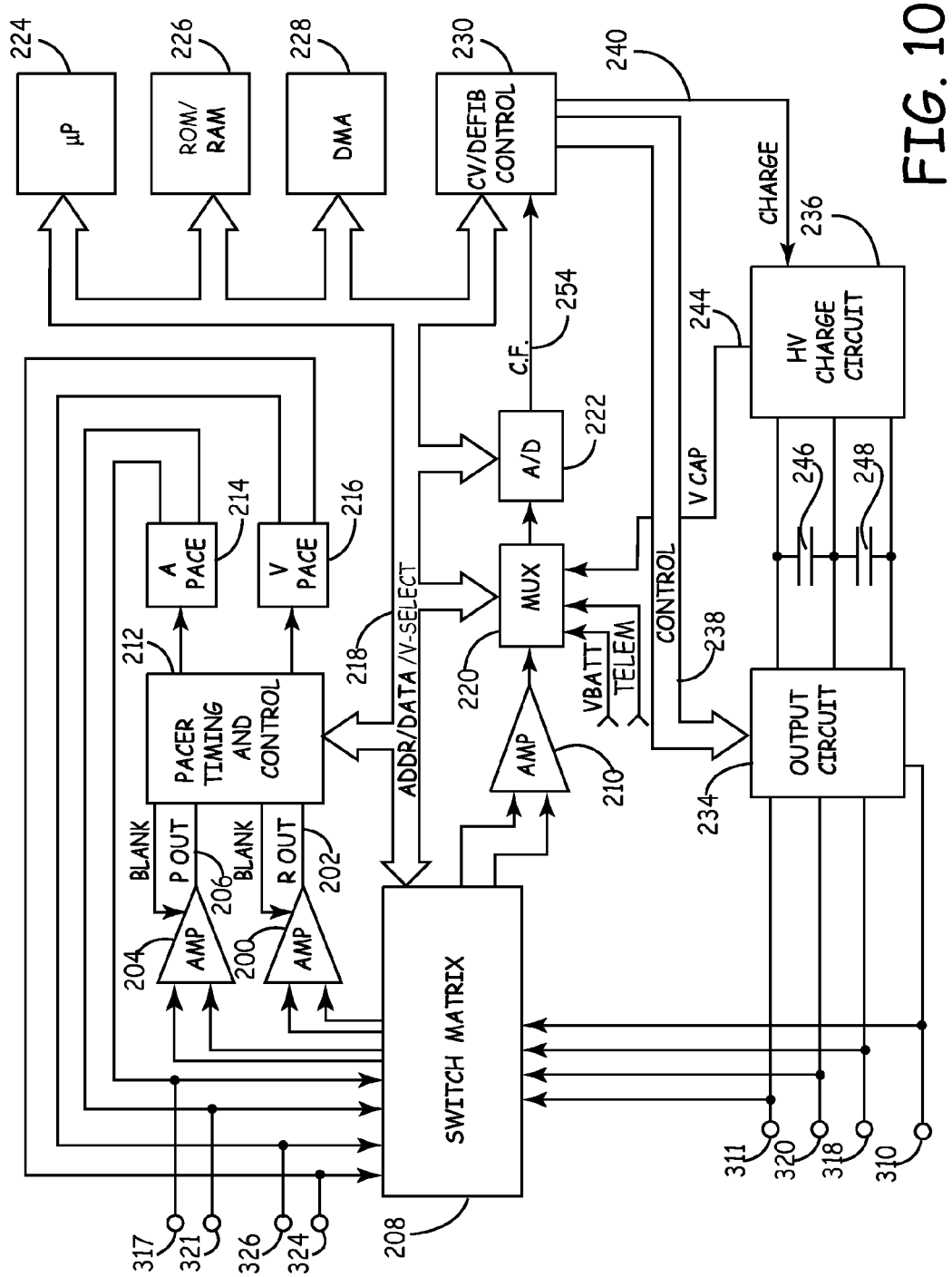
FIG. 10 is a block diagram of an ICD IPG in which the present invention may be practiced.

FIGS. 9 and 10 illustrate a dual chamber, multi-programmable, ICD IPG 400 and associated lead system for providing atrial and/or ventricular sensing functions for detecting P-waves of atrial depolarizations and/or R-waves of ventricular depolarizations, depending on the programmed pacing and/or sensing mode and delivering pacing or cardioversion/defibrillation therapies. An exemplary cardioversion/defibrillation lead system is depicted in FIG. 9 for delivering cardioversion/defibrillation shock therapies to the atria or ventricles of the heart. FIGS. 9 and 10 are intended to provide a comprehensive illustration of each of the atrial and/or ventricular, pacing and/or cardioversion/defibrillation configurations that may be effected using sub-combinations of the components depicted therein and equivalents thereto. The present invention can be implemented into such ICDs wherein the R-wave sense amplifier is normally blanked during a PAVBP following delivery of an A-PACE pulse.

In the preferred embodiment of FIGS. 9 and 10, depending on the programmed or current pacing mode, pacing pulses are applied to the atrium and/or ventricle in response to the detection of the appropriate bradycardia condition by the ICD IPG operating system. The pacing and sensing functions are effected through atrial and ventricular bipolar pace/sense electrode pairs at the ends of right atrial/superior vena cava (RA/SVC) and right ventricular (RV) leads 440 and 416, respectively, fixed in the right atrium 12 and right ventricle 16, respectively, that are electrically coupled to the circuitry of IPG 400 through a connector block 412. Delivery of cardioversion or defibrillation shocks to the atrial and/or ventricular chambers of the heart 10 may be effected through selected combinations of the illustrated exemplary RA and RV cardioversion/defibrillation electrodes on the RA/SVC and RV leads and an additional coronary sinus (CS) electrode on a CS lead 430 as well as an exposed surface electrode 410 of the outer housing or can of the IPG 400. The can electrode 410 optionally serves as a subcutaneous cardioversion/defibrillation electrode, used as one electrode optionally in combination with one intracardiac cardioversion/defibrillation electrode for cardioverting or defibrillating either the atria or ventricles. A remote, subcutaneous defibrillation patch electrode may be provided in addition to or substitution for the can electrode 410.

The RV lead 416 is depicted in a conventional configuration and includes an elongated insulating lead body, enclosing three concentric, electrically isolated, coiled wire conductors, separated from one another by tubular insulating sheaths. Located adjacent the distal end of the RV lead 416 are a pace/sense ring electrode 424, a helical, pace/sense electrode 426, mounted retractably within an insulating electrode head 428. Helical electrode 426 is adapted to be extended out of the electrode head 428 and screwed into the ventricular apex in a manner well known in the art. RV pace/sense electrodes 424 and 426 are each coupled to a coiled wire conductor within the RA lead body and are employed for cardiac pacing in the ventricle and for sensing near-field R-waves. RV lead 416 also supports an elongated, exposed wire coil, cardioversion/defibrillation electrode 422 in a distal segment thereof adapted to be placed in the right ventricle 16 of heart 10. The RV cardioversion/defibrillation electrode 422 may be fabricated from platinum, platinum alloy or other materials known to be usable in implantable cardioversion/defibrillation electrodes and may be about 5 cm in length. The cardioversion/defibrillation electrode 422 is also coupled to one of the coiled wire conductors within the lead body of RV lead 416. At the proximal end of the lead body is a bifurcated connector end 418 having three exposed electrical connectors, each coupled to one of the coiled conductors that are attached within the connector block 412 to connector block terminals in a manner well known in the art.

The coronary sinus (CS) lead 430 includes an elongated insulating lead body enclosing one elongated coiled wire conductor coupled to an elongated exposed coil wire cardioversion/defibrillation electrode 434. CS cardioversion/defibrillation electrode 434, illustrated in broken outline, is located within the coronary sinus and great vein 408 of the heart 10 and may be about 5 cm in length. At the proximal end of the CS lead 430 is a connector end 432 having an exposed connector coupled to the coiled wire conductor and attached within the connector block 412 to connector block terminals in a manner well known in the art.

The RA/SVC lead 440 includes an elongated insulating lead body carrying three concentric, electrically isolated, coiled wire conductors separated from one another by tubular insulating sheaths, corresponding generally to the structure of the RV lead 416. The lead body is formed in a manner well known in the art in an atrial J-shape in order to position its distal end in the right atrial appendage. A pace/sense ring electrode 444 and an extendable helical, pace/sense electrode 446, mounted retractably within an insulating electrode head 448, are formed distally to the bend of the J-shape. Helical electrode 446 is adapted to be extended out of the electrode head 448 and screwed into the atrial appendage in a manner well known in the art. RA pace/sense electrodes 444 and 446 are employed for atrial pacing and for near-field sensing of P-waves. An elongated, exposed coil defibrillation RA/SVC electrode 450 is supported on RA lead 440 extending proximally to pace/sense ring electrode 444 and coupled to the third coiled wire conductor within the RA lead body. Electrode 450 preferably is 40 cm in length or greater and is configured to extend from within the SVC and toward the tricuspid valve. At the proximal end of the RA lead 440 is a bifurcated connector 442 which carries three exposed electrical connectors, each coupled to one of the coiled wire conductors, that are attached within the connector block 412 to connector block terminals in a manner well known in the art.

Preferably, bipolar pace/sense electrodes 444, 446 and 424, 426 are employed for near field sensing and for delivery of pacing pulses to the atria and ventricles. The configuration, manner of fixation, and positioning of bipolar pace/sense electrodes 444, 446 and 424, 426 with respect to the atria and ventricles, respectively, may differ from those shown in FIG. 9. Unipolar pace/sense electrode bearing leads may also be used in the practice of the invention, and the second, return electrode may be one or more of the cardioversion/defibrillation electrodes or the can electrode 410.

The ICD system configuration and operating modes of FIG. 9 may be varied by eliminating: (1) the atrial or ventricular cardioversion/defibrillation capability and associated lead and electrodes while retaining the dual chamber pacing and sensing capability thereby providing single chamber cardioversion/defibrillation and dual chamber bradycardia/tachycardia pacing capabilities; or (2) in a special case of an atrial ICD, the ventricular cardioversion/defibrillation capability while retaining at least the atrial pace/sense capability and the ventricular sense capability for providing R-wave synchronization of the delivered atrial cardioversion therapies. In each such system, it will be understood that appropriate defibrillation and pacing leads will be employed in the system. In a simpler ICD system employing only the IPG can electrode 410 or a cardioversion/defibrillation electrode implanted subcutaneously and more remote from the heart chamber and only one the other of the cardioversion/defibrillation electrode located in proximity to the atrium or ventricle, e.g. electrodes 422 or 450, then it is desirable to couple the PVC sense amplifier inputs to the available cardioversion/defibrillation electrodes.

FIG. 10 is a functional schematic diagram of the circuitry of a dual chamber, ICD 400 in which the present invention may usefully be practiced. The circuitry of FIG. 10 should be taken as exemplary of a dual chamber ICD IPG 400 in which the invention may be embodied, and not as limiting, as it is believed that the invention may usefully be practiced in a wide variety of device implementations, as long as a dual chamber pacing mode providing bradycardia pacing therapies to the atria is retained that involve blanking of the ventricular sense amplifier.

The ICD IPG circuitry of FIG. 10 includes a high voltage section for providing relatively high voltage cardioversion/defibrillation shocks when needed in response to detection of a tachyarrhythmia, a low voltage pace/sense section for sensing P-waves and/or R-waves and providing relatively low voltage bradycardia pacing and anti-tachycardia pacing therapies, both operated under the control of a microcomputer including a microprocessor 224, ROM/RAM 226 and DMA 228. Other functions, including uplink and downlink telemetry with an external programmer for interrogating or programming operating modes and parameters, are also provided (but not shown) in a manner well known in the art.

The block diagram of FIG. 10 depicts the atrial and ventricular pace/sense and defibrillation lead connector terminals of the connector block 412. Assuming the electrode configuration of FIG. 9, the correspondence to the illustrated leads and electrodes is as follows: Optional terminal 310 is hard wired to can electrode 410, that is, the un-insulated portion of the housing of the ICD IPG 400, and technically may be directly connected and not be part of the connector block 412. Terminal 320 is adapted to be coupled through RV lead 416 to RV cardioversion/cardioversion/defibrillation electrode 422. Terminal 311 is adapted to be coupled through RA lead 440 to RA/SVC electrode 450. Terminal 318 is adapted to be coupled through CS lead 430 to CS cardioversion/defibrillation electrode 434. However, it will be understood that fewer terminals may be provided than depicted, and/or that one or more differing defibrillation leads, e.g. epicardial patch electrode and subcutaneous patch electrode bearing leads may also be employed for one or more of the depicted cardioversion/defibrillation electrode bearing leads.

Terminals 310, 311, 318 and 320 are coupled to high voltage output circuit 234. High voltage output circuit 234 includes high voltage switches controlled by CV/DEFIB CONTROL logic 230 via control bus 238. The switches within circuit 234 control which electrodes are employed and which are coupled to the positive and negative terminals of the capacitor bank including capacitors 246 and 248 during delivery of the intermediate and high voltage cardioversion and defibrillation shocks.

Terminals 324 and 326 of the connector block are adapted to be coupled through RV lead 416 to RV pace/sense electrodes 424 and 426 for sensing and pacing in the ventricle. Terminals 317 and 321 are adapted to be coupled through RA/SVC lead 440 to RA pace/sense electrodes 444 and 446 for sensing and pacing in the atrium. Terminals 324 and 326 are coupled to the inputs of R-wave sense amplifier 200 through switches in switch network 208. R-wave sense amplifier 200, which preferably takes the form of an automatic gain controlled amplifier providing an adjustable sensing threshold as a function of the measured R-wave signal amplitude. A VSENSE signal is generated on R-OUT line 202 whenever the signal sensed between electrodes 424 and 426 exceeds the current ventricular sensing threshold.

Terminals 317 and 321 are coupled to the P-wave sense amplifier 204 through switches in switch network 208. P-wave sense amplifier 204 preferably also takes the form of an automatic gain controlled amplifier providing an adjustable sensing threshold as a function of the measured P-wave amplitude. An ASENSE signal is generated on P-OUT line 206 whenever the signal sensed between pace/sense electrodes coupled to terminals 317, 321 exceeds the current atrial sensing threshold.

The A-PACE and V-PACE output circuits 214 and 216 are also coupled to terminals 317, 321 and 324, 326, respectively. The atrial and ventricular sense amplifiers 204 and 200 are isolated from the A-PACE and V-PACE output circuits 214 and 216 by appropriate isolation switches within switch matrix 208 and also by blanking circuitry operated by A-BLANK and V-BLANK signals during and for a short time following delivery of a pacing pulse in a manner well known in the art. One of the V-BLANK signals is the post atrial ventricular blanking signal provided during the PAVBP period as described above with reference to the dual chamber pacemaker IPG 100. The general operation of the R-wave and P-wave sense amplifiers 200 and 204 may correspond to that disclosed in U.S. Pat. No. 5,117,824, for example.

The ICD IPG circuitry of FIG. 10 provides atrial and/or ventricular cardiac pacing for bradycardia and tachycardia conditions and synchronized cardioversion and defibrillation shock therapies for tachyarrhythmias in accordance with therapy regimes programmed by the physician. With respect to the pacing operations, the pacer timing and control circuitry 212 includes programmable digital counters which control the basic time intervals associated with bradycardia pacing modes as is well known to the art.

In normal pacing modes of operation, e.g., the dual chamber pacing mode as set forth in FIG. 3, for example, intervals defined by pacer timing and control circuitry 212 include atrial and ventricular pacing escape intervals, blanking intervals, including the PAVBP, the refractory periods during which sensed P-waves and R-waves are ineffective to restart timing of the escape intervals, and the pulse widths of the pacing pulses. These intervals are determined by microprocessor 224, in response to stored data in RAM in ROM/RAM 226 and are communicated to the pacer timing and control circuitry 212 via address/data bus 218. Pacer timing and control circuitry 212 also determines the amplitude of the cardiac pacing pulses under control of microprocessor 224.

During pacing, the escape interval counters within pacer timing and control circuitry 212 are reset upon sensing of R-waves and P-waves as indicated by a signals on lines 202 and 206. In accordance with the selected pacing mode, pacer timing and control circuitry 212 provides pace trigger signals to the A-PACE and V-PACE output circuits 214 and 216 on timeout of the appropriate escape interval counters to trigger generation of atrial and/or ventricular pacing pulses. The pacing escape interval counters are also reset on generation of A-PACE and R-PACE pulses, and thereby control the basic timing of cardiac pacing functions.

Pacer timing and control circuitry 212 also controls escape intervals associated with timing and delivering anti-tachyarrhythmia pacing in both the atrium and the ventricle, employing any anti-tachyarrhythmia pacing therapies known to the art. The value of the counts present in the escape interval counters when reset by sensed R-waves and P-waves may be used as measures of the durations of R-R intervals, P-P intervals, P-R intervals and R-P intervals, which measurements are stored in RAM in ROM/RAM 226 and used to detect the presence of tachyarrhythmias as described below.

Microprocessor 224 operates as an interrupt driven device, and is responsive to interrupts from pacer timing and control circuitry 212 corresponding to the occurrence sensed P-waves (ASENSE) and R-waves (VSENSE) and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of RAM in the ROM/RAM 226 (FIG. 10) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time.

In the event that an atrial or ventricular tachyarrhythmia is detected, and an anti-tachyarrhythmia pacing regimen is prescribed, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation shock is required, microprocessor 224 employs the an escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246 and 248 via charging circuit 236, under control of high voltage charging control line 240. The voltage on the high voltage capacitors is monitored via VCAP line 244, and the monitored voltage signal is passed through multiplexer 220, digitized, and compared to a predetermined value set by microprocessor 224 in ADC/comparator 222. When the voltage comparison is satisfied, a logic signal on Cap Full (CF) line 254 is applied to cardioversion/defibrillation control circuit 230, terminating charging. Thereafter, timing of the delivery of the defibrillation or cardioversion shock is controlled by pacer timing/control circuitry 212. Following delivery of the fibrillation or tachycardia therapy, the microprocessor 224 then returns the operating mode to cardiac pacing and awaits the next successive interrupt due to pacing or the occurrence of a sensed atrial or ventricular depolarization.

In the illustrated ICD operating system, delivery of the cardioversion or defibrillation shocks is accomplished by output circuit 234, under control of control circuitry 230 via control bus 238. Output circuit 234 determines whether a monophasic or biphasic shock is delivered, the polarity of the electrodes and which electrodes are involved in delivery of the shock. Output circuit 234 also includes high voltage switches that control whether electrodes are coupled together during delivery of the shock. Alternatively, electrodes intended to be coupled together during the shock may simply be permanently coupled to one another, either exterior to or interior of the device housing, and polarity may similarly be pre-set, as in current implantable defibrillators. An example of output circuitry for delivery of biphasic shock regimens to multiple electrode systems may be found in U.S. Pat. No. 4,727,877, for example.

In accordance with the present invention, a PVC sense amplifier 210 is incorporated into the circuitry of FIG. 10 having a pair of sense inputs that can be selectively coupled through switches within switch network 208 in response to a programmed V-SELECT command received through bus 218 to a pair of PVC sense electrodes selected from among the depicted electrodes, preferably from among cardioversion/defibrillation electrodes 422, 434, 450, can electrode 410, and one of the ring pace-sense electrode 424 and the tip pace/sense electrode 426. Switch matrix 208 is used in the PVC sensing function of the present invention to select which pair of the available pace/sense and/or cardioversion/defibrillation electrodes is coupled to the inputs of wide band (0.5-200 Hz) PVC sense amplifier 210 for use in detecting PVCs during the PAVBP (and at other times during the cardiac cycle). A PVC signal from bandpass amplifier 210 is passed through multiplexer 220 and may be converted to multi-bit digital signals by ND converter 222, for storage in RAM in ROM/RAM 226 under control of DMA 228. The microprocessor 224 may employ digital signal and morphology analysis techniques to characterize the digitized signals stored in ROM/RAM 226 to recognize and classify the patient's heart rhythm employing any of the numerous signal processing methodologies known to the art.

In a dual chamber pacing mode involving atrial pacing and ventricular sensing, the PVC amplifier 210 is not blanked during the PAVBP. The steps set forth in FIGS. 3 and 4 are followed. A PVC that is detected during time-out of a PAV is employed as an interrupt to the microprocessor 224 in step S130. The steps of FIG. 4 are followed to determine whether to inhibit the delivery of a V-PACE pulse upon time-out of the PAV delay or to deliver a V-PACE upon time out of a VSP delay.

In this embodiment illustrated in FIGS. 9 and 10, the PVC sense vector can be selected by an appropriate V-SELECT command among: (1) the can electrode 410 and the RV coil cardioversion/defibrillation electrode 422; (2) the can electrode 410 and the SVC coil cardioversion/defibrillation electrode 450; (3) the can electrode 410 and the RV ring pace/sense electrode 424; (4) the can electrode 410 and the CS coil cardioversion/defibrillation electrode 434; (5) the CS coil cardioversion/defibrillation electrode 434 and the RV ring pace/sense electrode 424; (6) the CS coil cardioversion/defibrillation electrode 434 and the RV coil cardioversion/defibrillation electrode 422; and (7) the RV coil cardioversion/defibrillation electrode 422 and the SVC coil cardioversion/defibrillation electrode 450.

Advantageously, the PVC sense amplifiers within the sense amplifiers circuits 360, 360', and 360" and the PVC sense amplifier 210 and can be enabled during the cardiac cycle to function as a conventional EGM sense amplifier so that the spontaneously occurring PQRST complexes can be recorded for real time analysis or data storage as is well known in the art.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. A pacing system comprising:
   an implantable pulse generator, an atrial lead coupled to the implantable pulse generator having at least one active atrial pace/sense electrode adapted to be disposed in operative relation to an atrial heart chamber, at least one indifferent atrial pace/sense electrode adapted to be implanted in the patient's body, a ventricular lead coupled to the implantable pulse generator having at least one active ventricular pace/sense electrode adapted to be disposed in operative relation to a ventricular heart chamber, and an indifferent ventricular pace/sense electrode adapted to be implanted in the patient's body;
   means for generating atrial pace (A-PACE) pulses;
   means for sensing a natural ventricular depolarization;
   means for producing a V-EVENT signal upon sensing a natural ventricular depolarization;
   means for generating ventricular pace (V-PACE) pulses;
   V-A interval timing means for timing out a V-A interval following generation of a V-PACE pulse and following sensing of a V-EVENT;
   means for triggering said atrial pace generating means to generate an A-PACE pulse following expiration of the V-A interval;
   means for timing out a PAV interval upon triggering of said atrial pace generating means;
   means for timing a ventricular blanking period following generation of an atrial pace pulse (A-PACE);
   means for inhibiting said V-EVENT signal producing means during the ventricular blanking period following generation of an atrial pace pulse (A-PACE);
   a PVC sense electrode pair spatially separated from the ventricular pace/sense electrodes;
   sensing means coupled to the PVC sense electrode pair for generating a signal indicating occurrence of a PVC, as a PVC declaration signal, by sensing of a depolarization of the ventricles occurring during the ventricular blanking period; and
   means responsive to the generation of a PVC declaration signal for terminating the PAV delay and triggering the V-A interval timing means to time out the V-A interval.

2. The pacing system of claim 1, further comprising:
means for timing a ventricular safety pace delay from the delivery of an A-PACE pulse; and
means responsive to a declaration of a PVC for triggering the ventricular pace means to generate and deliver a V-PACE pulse through the active and indifferent ventricular pace/sense electrodes upon time-out of the ventricular safety pace delay.

3. The pacing system of claim 2, wherein the ventricular safety pace delay is longer than the ventricular blanking period and is shorter than the PAV delay and is selected to ensure that the delivered V-PACE pulse is not delivered into the vulnerable period of the heart.

4. The pacing system of claim 1, further comprising:
atrial sensing means coupled to the active and indifferent atrial pace/sense electrodes for sensing natural atrial depolarizations and declaring an A-EVENT;
means for terminating the V-A interval upon declaration of an A-EVENT during time-out of the V-A interval; and
means for timing out an SAV interval upon declaration of an A-EVENT during time-out of the V-A interval.

5. The pacing system of claim 1, further comprising:
means for timing a ventricular safety pace delay from the delivery of an A-PACE pulse, the ventricular safety pace delay is longer than the ventricular blanking period and is shorter than the PAV delay and is selected to ensure that the delivered V-PACE pulse is not delivered into the vulnerable period of the heart; and
means responsive to a declaration of a PVC during the ventricular safety pace delay for triggering the ventricular pace pulse generating means to generate and deliver a V-PACE pulse through the active and indifferent ventricular pace/sense electrodes to the ventricular heart chamber upon time-out of the ventricular safety pace delay.

6. The pacing system of claim 1, wherein:
the active and indifferent ventricular pace/sense electrodes are disposed on the ventricular lead; and
the PVC sense electrode pair comprises an indifferent pace/sense electrode disposed on the implantable pulse generator and one of the active and indifferent ventricular pace/sense electrodes are disposed on the ventricular lead.

7. The pacing system of claim 1, wherein:
the implantable pulse generator comprises a housing supporting at least two sense electrodes in a sense electrode array; and
the PVC sense electrode pair comprises the sense electrodes supported by the implantable pulse generator housing.

8. The pacing system of claim 1, wherein the implantable pulse generator comprises a housing supporting at least three sense electrodes in a sense electrode array, and further comprising:
means of selecting the PVC sense electrode pair from among the at least three sense electrodes supported by the implantable pulse generator housing.

9. The pacing system of claim 1, further comprising a first and second cardioversion/defibrillation electrodes disposed about one of the atria and the ventricles for delivering cardioversion/defibrillation shocks to the heart chamber, and wherein:
the implantable pulse generator further comprises means for determining the existence of a tachyarrhythmia and providing cardioversion/defibrillation shock therapy through the first and second cardioversion/defibrillation electrodes; and
the PVC sense electrodes include at least one of the first and second cardioversion/defibrillation electrodes.

10. The pacing system of claim 9, wherein the PVC sense electrodes include the first and second cardioversion/defibrillation electrodes.

11. The pacing system of claim 1, wherein:
the atrial lead supports a first cardioversion/defibrillation electrode adapted to be disposed in relation to the heart, and the ventricular lead supports a second cardioversion/defibrillation electrode adapted to be disposed in relation to the heart;
the implantable pulse generator further comprises means for determining the existence of a tachyarrhythmia and providing cardioversion/defibrillation shock therapy through the first and second cardioversion/defibrillation electrodes; and
the PVC sense electrodes include at least one of the first and second cardioversion/defibrillation electrodes.

12. The pacing system of claim 11, wherein the PVC sense electrodes include the first and second cardioversion/defibrillation electrodes.

13. The pacing system of claim 1, further comprising a coronary sinus lead extending from the implantable pulse generator supporting a first cardioversion/defibrillation electrode adapted to be disposed in relation to a left heart chamber of the heart, and wherein:
the ventricular lead supports a second cardioversion/defibrillation electrode adapted to be disposed in relation to the right ventricle of the heart;
the implantable pulse generator further comprises means for determining the existence of a tachyarrhythmia and providing cardioversion/defibrillation shock therapy through the first and second cardioversion/defibrillation electrodes; and
the PVC sense electrodes include at least one of the first and second cardioversion/defibrillation electrodes.

14. The pacing system of claim 13, wherein the PVC sense electrodes include the first and second cardioversion/defibrillation electrodes.

15. The pacing system of claim 1, further comprising a coronary sinus lead extending from the implantable pulse generator supporting a left heart chamber pace/sense electrode adapted to be disposed in relation to a left heart chamber of the heart, and wherein:
the implantable pulse generator further comprises means for providing synchronized pacing of right and left heart chambers through the atrial and ventricular pace/sense electrodes and the left heart chamber pace/sense electrode; and
the PVC sense electrodes include the left heart chamber pace/sense electrode.

16. The pacing system of claim 15, wherein the PVC sense electrodes include the left heart chamber pace/sense electrode and one of the active and indifferent ventricular pace/sense electrodes.

17. The pacing system of claim 15, wherein the PVC sense electrodes include the left heart chamber pace/sense electrode and an indifferent pace/sense electrode disposed on the implantable pulse generator.

18. A pacing system comprising:
an atrial electrode, a ventricular electrode and a PVC sensing electrode, spatially separated from one another and all coupled to an implantable pulse generator, the implantable pulse generator comprising:
an atrial pulse generator coupled to the atrial electrode;

a ventricular blanking timer initiated responsive to the atrial pulse generator, initiated responsive to generation of an atrial pacing pulse; and a V-A interval timer responsive to and initiated by signals sensed on the ventricular electrode after but not during timeout of the ventricular blanking timer and triggering generation of an atrial pacing pulse on expiration of the V-A interval; wherein the V-A interval timer is further responsive to and initiated by signals sensed on the PVC sense electrode during timeout of the ventricular blanking timer.

19. The system of claim 18 wherein the PVC sense electrode comprises an electrode located on a transvenous lead.

20. The system of claim 18 wherein the PVC sense electrode comprises an electrode located on a subcutaneous lead.

21. The system of claim 18 wherein the ventricular electrode comprises an electrode located on a left ventricular lead.

22. The system of claim 18 wherein the ventricular electrode comprises an electrode located on a right ventricular lead.

23. The system of claim 18 wherein:

the V-A interval timer is further responsive to and initiated by signals sensed on the PVC sense electrode after the timeout of the ventricular blanking timer.

24. The system of claim 18 wherein the ventricular blanking interval is 400 milliseconds or less.

25. The system of claim 18 wherein the ventricular blanking interval is about 30 milliseconds.

26. The system of claim 18 further comprising:

a ventricular pulse generator coupled to the ventricular electrode;

a ventricular safety pacing interval timer responsive to and triggered by the atrial pulse generator; and a ventricular safety pacing flag set in response to signals sensed on the PVC sense electrode during ventricular safety pacing interval timeout;

and wherein the ventricular pulse generator is responsive to and triggered by expiration of the ventricular safety pacing interval if the ventricular safety pacing flag was set during the ventricular safety pacing interval.

27. The system of claim 26 further comprising:

an A-V pacing interval timer responsive to the atrial pulse generator and initiated by generation of an atrial pacing pulse;

wherein the ventricular pulse generator is responsive to and triggered by the expiration of the A-V pacing interval; and wherein the pace A-V interval interval timer is responsive to and timing of the A-V interval is terminated by signals sensed on the PVC sense electrode after expiration of the ventricular safety pacing interval.

* * * * *